(12) United States Patent
Sakane

(10) Patent No.: US 11,373,422 B2
(45) Date of Patent: Jun. 28, 2022

(54) EVALUATION ASSISTANCE METHOD, EVALUATION ASSISTANCE SYSTEM, AND COMPUTER-READABLE MEDIUM

(71) Applicant: OLYMPUS CORPORATION, Tokyo (JP)

(72) Inventor: Isao Sakane, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 11 days.

(21) Appl. No.: 16/930,793

(22) Filed: Jul. 16, 2020

(65) Prior Publication Data

US 2021/0019580 A1 Jan. 21, 2021

(30) Foreign Application Priority Data

Jul. 17, 2019 (JP) .............................. JP2019-131832

(51) Int. Cl.
*G06K 9/62* (2022.01)
*G06V 10/25* (2022.01)
*G06V 10/40* (2022.01)
*G06V 30/194* (2022.01)

(52) U.S. Cl.
CPC ................................. *G06V 30/194* (2022.01)

(58) Field of Classification Search
CPC . G06K 9/00127; G06K 9/4604; G06K 9/6267
See application file for complete search history.

(56) References Cited

U.S. PATENT DOCUMENTS

| 2012/0170835 | A1* | 7/2012 | Wang | G06K 9/6265 |
| | | | | 382/159 |
| 2015/0242676 | A1 | 8/2015 | Barlaud | |
| 2018/0365565 | A1* | 12/2018 | Panciatici | G06T 17/00 |
| 2019/0130216 | A1* | 5/2019 | Tomioka | G06K 9/6267 |
| 2019/0221313 | A1* | 7/2019 | Rim | G16H 10/60 |
| 2019/0340470 | A1* | 11/2019 | Hsieh | G06K 9/4604 |
| 2019/0377972 | A1* | 12/2019 | Liu | G06K 9/627 |
| 2020/0134446 | A1* | 4/2020 | Soni | G06N 3/08 |
| 2020/0349466 | A1* | 11/2020 | Hoogerwerf | G06N 3/08 |

FOREIGN PATENT DOCUMENTS

| JP | 2011-229413 A | 11/2011 |
| JP | 2015-508501 A | 3/2015 |
| JP | 2018-097671 A | 6/2018 |
| JP | 2018-205069 A | 12/2018 |

* cited by examiner

*Primary Examiner* — Oneal R Mistry
(74) *Attorney, Agent, or Firm* — Scully, Scott, Murphy & Presser, P.C.

(57) ABSTRACT

An evaluation assistance method includes: acquiring a first image to be used for performance evaluation of trained models; generating a plurality of second images, each of the plurality of second images being a result of processing the first image by each of a plurality of trained models; and displaying each of the plurality of trained models in association with a corresponding second image of the plurality of second images.

20 Claims, 33 Drawing Sheets

EVALUATION ASSISTANCE METHOD, EVALUATION ASSISTANCE SYSTEM, AND COMPUTER-READABLE MEDIUM

CROSS REFERENCE TO RELATED APPLICATIONS

This application is based upon and claims the benefit of priority from prior Japanese Patent Application No. 2019-131832, filed Jul. 17, 2019, the entire contents of which are incorporated herein by this reference.

BACKGROUND OF THE INVENTION

Field of the Invention

Disclosures herein are related to an evaluation assistance method, an evaluation assistance system, and a computer-readable medium.

Description of the Related Art

In recent years, machine learning has attracted attention in various technical fields. In the technical field of pathological diagnosis, the burden on pathologists is expected to be reduced using trained learning models that have been trained to recognize lesions (hereinafter, "trained models"). In the technical field of cell culture, cells under cultivation are expected to be examined in a non-destructive manner using trained models that have been trained to recognize cell states. For example, examining the state of differentiation or undifferentiation of iPS cells in a non-destructive manner so as to grasp the growth state may allow a schedule for a surgery using iPS cells to be more appropriately determined.

Techniques pertaining to such machine learning is described in, for example, Japanese Laid-open Patent Publication No. 2011-229413. Japanese Laid-open Patent Publication No. 2011-229413 describes a technique for assisting the building of a trained model. Using the technique described in Japanese Laid-open Patent Publication No. 2011-229413, even a person who does not have an advanced knowledge on machine learning can build a trained model relatively easily.

SUMMARY OF THE INVENTION

An evaluation assistance method in accordance with an aspect of the present invention includes: acquiring a first image to be used for performance evaluation of trained models; generating a plurality of second images, the plurality of second images each being a result of processing the first image by each of a plurality of trained models; and displaying each of the plurality of trained models in association with a corresponding second image of the plurality of second images.

A trained model evaluation assistance system in accordance with an aspect of the invention includes: a non-transitory computer-readable storage medium storing a plurality of trained models; and at least one processor, wherein the processor performs the processes of: acquiring a first image to be used for performance evaluation of trained models; generating a plurality of second images, the plurality of second images each being a result of processing the first image by each of a plurality of trained models; and displaying each of the plurality of trained models in association with a corresponding second image of the plurality of second images.

A computer-readable medium in accordance with an aspect of the invention is a non-transitory computer-readable medium having a program stored therein, the program causing a computer to perform the procedures of: acquiring a first image to be used for performance evaluation of trained models; generating a plurality of second images, the plurality of second images each being a result of processing the first image by each of a plurality of trained models; and displaying each of the plurality of trained models in association with a corresponding second image of the plurality of second images.

DETAILED DESCRIPTION OF THE PREFERRED EMBODIMENTS

While there are services for assisting the building of trained models, there are also services for providing trained models. The troubles of building trained model can be saved using trained models provided by others.

However, it will not be necessarily easy to determine whether a trained model is good or bad. For example, standards for determining whether a cell is alive may not be always uniform. Thus, a trained model trained to determine whether a cell is alive may be good for a certain user but may be insufficiently good for another user.

In view of such a fact, the following describes embodiments of the present invention.

Figure 1:
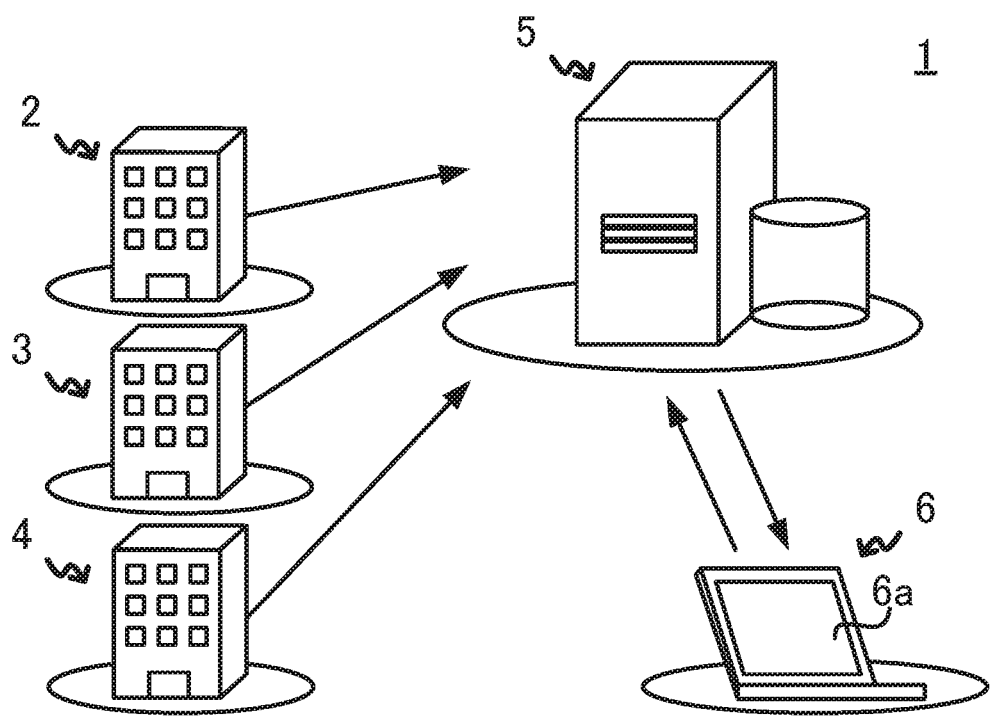
FIG. 1 illustrates an example of the configuration of a system 1.

FIG. 1 illustrates an example of the configuration of a system 1. The system 1 depicted in FIG. 1 is an evaluation assistance system for assisting evaluation of a trained model. The system 1 includes model providing apparatuses (model providing apparatuses 2, 3, 4 . . . ), a service providing apparatus 5, and a usage apparatus 6.

The model providing apparatuses provide trained models. For example, the model providing apparatuses may be computers connected to a communication network. The model providing apparatuses provide the service providing apparatus 5 with one or more trained models.

The service providing apparatus 5 provides services for assisting evaluation of a trained model provided by the model providing apparatus. For example, the service providing apparatus 5 may be a computer connected to the communication network. The service providing apparatus 5 may include a non-transitory computer-readable storage medium storing a plurality of trained models and at least one processor.

The usage apparatus 6 uses evaluation assistance services provided by the service providing apparatus 5 and also uses a trained model provided from the model providing apparatus to the service providing apparatus 5. The usage apparatus 6 includes a display apparatus 6a. The usage apparatus 6 displays, on the display apparatus 6a, screen information for assisting evaluation of a trained model provided from the service providing apparatus 5, thereby allowing the user of the usage apparatus 6 to evaluate the trained model under his/her standards.

Figure 2:
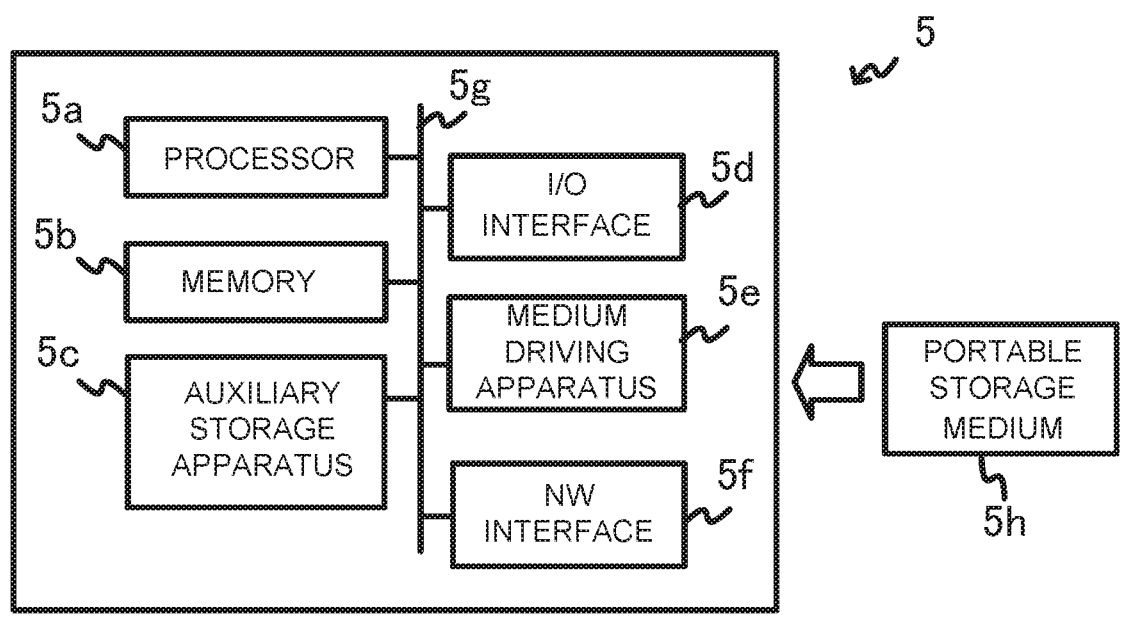
FIG. 2 illustrates an example of the hardware configuration of a service providing apparatus 5.

FIG. 2 illustrates an example of the hardware configuration of the service providing apparatus 5. For example, a processor 5a may be an arbitrary processing circuit including a central processing unit (CPU) and perform a programmed process by loading a program stored in an auxiliary storage apparatus 5c or a portable storage medium 5h into a memory 5d for execution. The processor 5a may include a graphics processing unit (GPU). The processor 5a performs a programmed process by executing a program so as to perform, for example, an evaluation assistance process described hereinafter.

The memory 5b is, for example, a random access memory (RAM). In program execution, the memory 5b functions as a work memory for storing a program or data stored in the auxiliary storage apparatus 5c or the portable storage medium 5h. The auxiliary storage apparatus 5c is, for example, a hard disk or a flash memory and is used mainly to store various data and programs. A medium driving apparatus 5e accommodates the portable storage medium 5h, such as an optical disc or Compact Flash®. The auxiliary storage apparatus 5c and the portable storage medium 5h are each an example of a non-transitory computer-readable storage medium storing a program.

For example, an input/output (I/O) interface 5d may be a universal-serial-bus (USB) interface circuit or a high-definition multimedia interface (HDMI) circuit. The I/O interface 5d may have, for example, an input apparatus (not illustrated), a display apparatus (not illustrated), or the like connected thereto.

For example, a network (NW) interface 5f may be a radio communication module or a local-area-network (LAN) card. The service providing apparatus 5 receives a trained model from the model providing apparatus via the NW interface 5f and transmits, to the usage apparatus 6 via the NW interface 5f, screen information required for the providing of services.

The configuration depicted in FIG. 2 is an example of the hardware configuration of the service providing apparatus 5, and the service providing apparatus 5 is not limited to this configuration. The service providing apparatus 5 may be a special-purpose apparatus, rather than a general-purpose apparatus. For example, the service providing apparatus 5 may include a specifically designed electric circuit, e.g., an application specific integrated circuit (ASIC). The service providing apparatus 5 may be configured using a field-programmable gate array (FPGA).

Figure 3:
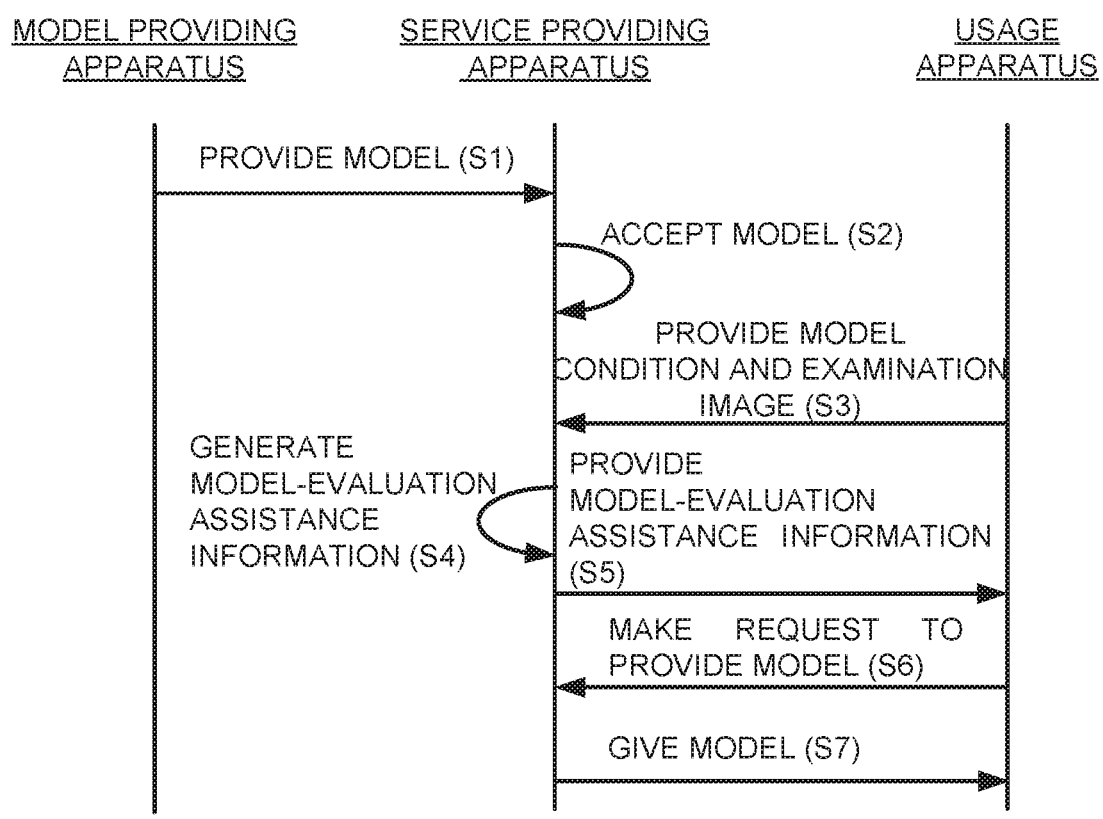
FIG. 3 is an example of a sequence diagram for illustrating services provided by a system 1.
Figure 4:
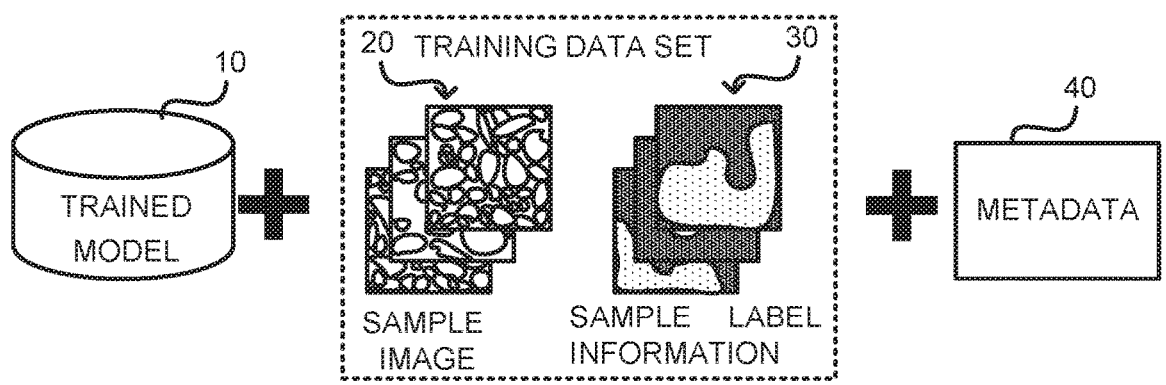
FIG. 4 is an explanatory diagram for data provided by a model providing apparatus.
Figure 5:
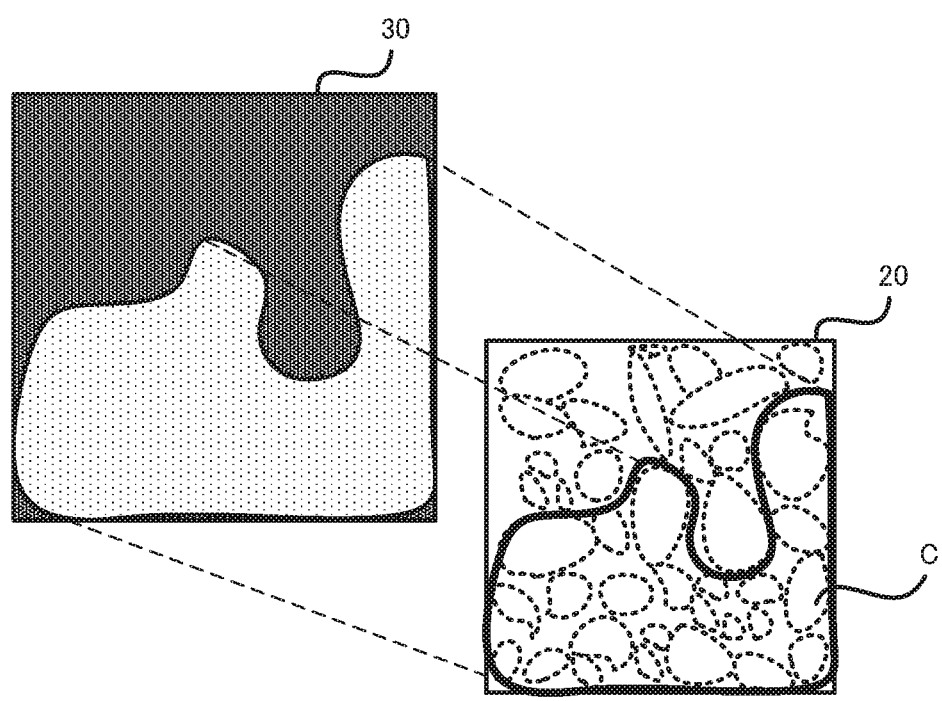
FIG. 5 is an explanatory diagram for sample label information 30.
Figure 6:
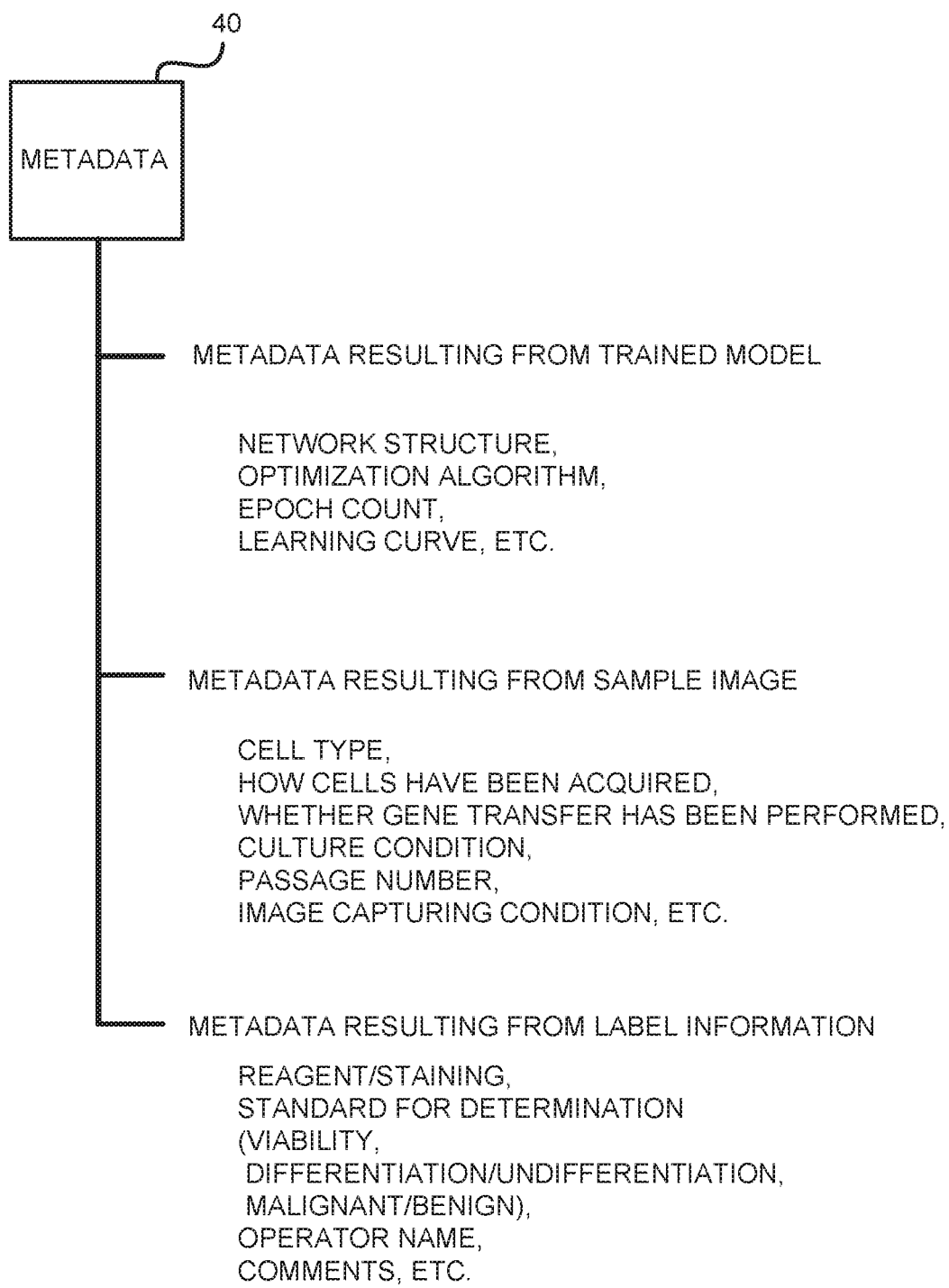
FIG. 6 is an explanatory diagram for metadata 40.

FIG. 3 is an example of a sequence diagram for illustrating services provided by the system 1. FIG. 4 is an explanatory diagram for data provided by the model providing apparatus. FIG. 5 is an explanatory diagram for sample label information 30. FIG. 6 is an explanatory diagram for metadata 40. By referring to FIGS. 3-6, the following describes a trained model evaluation assistance method implemented by the system 1.

In the system 1, the model providing apparatus first provides the service providing apparatus 5 with a trained model (step S1). As an acceptance condition, the service providing apparatus 5 has made in advance a request for the model providing apparatus to provide a training data set and metadata together with a trained model. Thus, in step S1, the model providing apparatus provides the service providing apparatus 5 with a training data set and metadata 40 in addition to a trained model 10 in accordance with the acceptance condition, as depicted in FIG. 4. The training data set includes a sample image 20 and sample label information 30.

A trained model refers to a learning model that has been trained using a training image and correct answer information corresponding to the training image. In particular, a trained model is a learning model trained so that an output associated with an input of a training image is close to correct answer information corresponding to the training image and it is a model in which an output associated with an input of a validation image has been validated to be close to correct answer information corresponding to the validation image.

The trained model 10 provided by the service providing apparatus 5 in step S1 is a trained model for image recognition and, for example, may be, but is not particularly limited to, a trained model using deep learning. The following descriptions are given by referring to an example in which a trained model 10 is a model for predicting and identifying a certain region included in an image. More specifically, descriptions are given by referring to an example in which the trained model 10 outputs identification information identifying a prediction region which is predicted to be a positive or negative region included in an image. For example, for a trained model that identifies the differentiation state of iPS cells, a differentiated region in the iPS cells may correspond to a positive region, and an undifferentiated region in the iPS cells may correspond to a negative region. The trained model may be a model for determining a cell detachment or a model for a viability determination (life or death determination) for cells.

The service providing apparatus 5 provides one or more sample images 20 used in the training process for the trained model 10, and desirably a plurality of sample images 20 are provided. Sample images 20 may be some (e.g., 10) of the plurality of images used in the training process for a trained model 10. A sample image 20 may be a training image used in a training process or a validation image used in the training process. Sample images 20 may include both training images and validation images.

The sample label information 30 provided by the service providing apparatus 5 is correct answer information used in the training process for the trained model 10 and indicates a correct answer as an output associated with an input of the sample image 20. In particular, sample label information 30 is identification information for identifying a correct answer region C that is a positive or negative region included in the sample image 20, as depicted in FIG. 5. Sample label information 30 may be correct answer information corresponding to a training image or correct answer information corresponding to a validation image. Sample label information 30 may include both correct answer information corresponding to a training image and correct answer information corresponding to a validation image. For example, sample label information 30 may be generated by a model provider manually specifying a region. For a sample image 20 that is a microscopic image, sample label information 30 may be an image generated by capturing an image of a fluorescently stained sample. For a sample image 20 acquired by a flexible endoscope or a rigid endoscope, sample label information 30 may be generated by capturing an image of an iodine-stained or methylene-blue-stained (MB-stained) sample. For a sample image 20 acquired by a narrow-band-imaging (NBI) endoscope, sample label information 30 may be information simulating the NBI endoscope signal.

The metadata 40 provided by the service providing apparatus 5 may be metadata resulting from a trained model 10 or metadata resulting from a sample image 20, as depicted in FIG. 6. Alternatively, metadata 40 may be metadata resulting from sample label information 30. Metadata resulting from a trained model 10 may be a network structure, an optimization algorithm, or an epoch count when, for example, the trained model 10 uses deep learning. Metadata resulting from a sample image 20 may be, for example, a cell type, how cells have been acquired, whether gene transfer has been performed, or a culture condition. Information on an apparatus that has acquired a sample 20, e.g., image capturing condition, apparatus type, microscopy, is also an example of metadata resulting from the sample image 20. For a medical image, the name of a given organ, the name or identification number of a subject, information on an applied diagnostic guideline may be used as metadata. In addition, an image size or the number of images may be provided as metadata. Metadata resulting from sample label information 30 may be information on whether a reagent or staining has been used, information on a reagent or staining condition, a standard for determining whether a region is positive or negative, or an operator name. In addition, metadata 40 may be metadata resulting from a model providing apparatus and include, for example, creator information specifying a company, research institute, or university that has built a trained model 10.

Metadata 40 is not limited to the examples described above. Metadata 40 is used when the service providing apparatus 5 selects a trained model 10 to be provided to the usage apparatus 6, as will be described hereinafter. Thus, the service providing apparatus 5 may make, as an acceptance condition, a request for the model providing apparatus to incorporate arbitrary information that can contribute to selection of a trained model 10 into metadata 40.

When a trained model is provided from the model providing apparatus, the service providing apparatus 5 accepts the provided trained model (step S2). In this case, the service providing apparatus 5 accepts and registers a training data set and metadata 40 as well as the trained model 10 in a database built in a non-transitory computer-readable storage medium.

The trained model 10 is desirably converted to a compatible format before registration in the database. In this way, trained models 10 built using various frameworks under various model providing apparatuses can be operated on a framework used by the service providing apparatus 5 and the usage apparatus 6. The service providing apparatus 5 desirably repeatedly accepts models provided from a plurality of model providing apparatuses. In this way, a plurality of trained models 10 will be registered in the database of the service providing apparatus 5.

Afterward, to find a trained model fitting a purpose of the user of the usage apparatus 6 from the trained models 10 registered in the service providing apparatus 5, the usage apparatus 6 provides the service providing apparatus 5 with a condition that a trained model is required to satisfy and an examination image to be examined by the trained model (step S3). There may be one or more examination images. The examination image is an example of a first image to be used for performance evaluation of a trained model 10. Step S3 is an example of the process of acquiring a first image to be used for performance evaluation of a trained model. The following descriptions are given by referring to an example in which an examination image is an image of cells acquired by a microscope, but an examination image is not limited to an image of cells acquired by a microscope. For example, an examination image may be an image of an organ in the body cavity acquired by an endoscope. The endoscope may be a flexible endoscope, a rigid endoscope, or an NBI endoscope. An image of cells acquired by the microscope may be an image of cultured cells or an image of cells collected from a subject that is to be used in a pathological diagnosis. Images may be acquired by the microscope using any type of microscopy. For example, images may be acquired using fluorescent microscopy, bright field microscopy, dark field microscopy, phase difference microscopy, differential interference contrast microscopy, or polarization microscopy.

When the examination image and the condition that a trained model is required to satisfy are provided from the usage apparatus 6, the service providing apparatus 5 generates model-evaluation assistance information (step S4). In this case, the service providing apparatus 5 searches metadata registered in the database on the basis of the condition that a trained model is required to satisfy and extracts a plurality of trained models meeting the condition that a trained model is required to satisfy according to demand from the usage apparatus 6. In addition, the service providing apparatus 5 applies the examination image to the plurality of extracted trained models so as to generate model-evaluation assistance information that includes a plurality of examination results for the examination image. Note that model-evaluation assistance information is information for assisting the usage apparatus 6 evaluating a trained model.

Upon generating model-evaluation assistance information, the service providing apparatus 5 provides the usage apparatus 6 with the model-evaluation assistance information (step S5). Then, by referring to the model-evaluation assistance information displayed on the display apparatus 6*a* of the usage apparatus 6, the user of the usage apparatus 6 selects a trained model fitting the user's purpose from the trained models presented by the service providing apparatus 5. The usage apparatus 6 makes a request for the service providing apparatus 5 to provide the trained model selected by the user (step S6). Finally, the service providing apparatus 5 gives the usage apparatus 6 the trained model requested by the usage apparatus 6 (step S7).

In the system 1, as described above, the service providing apparatus 5 generates a plurality of examination results by applying an examination image specified by the usage apparatus 6 as an object to be examined to a plurality of trained models and provides the usage apparatus 6 with these examination results. Thus, by comparing the plurality of examination results, the user of the usage apparatus 6 can evaluate the plurality of trained models registered in the service providing apparatus 5 according to the user's standard. The following describes specific examples of the processes of steps S3-S5 in FIG. 3 in detail with reference to embodiments.

First Embodiment

Figure 7:
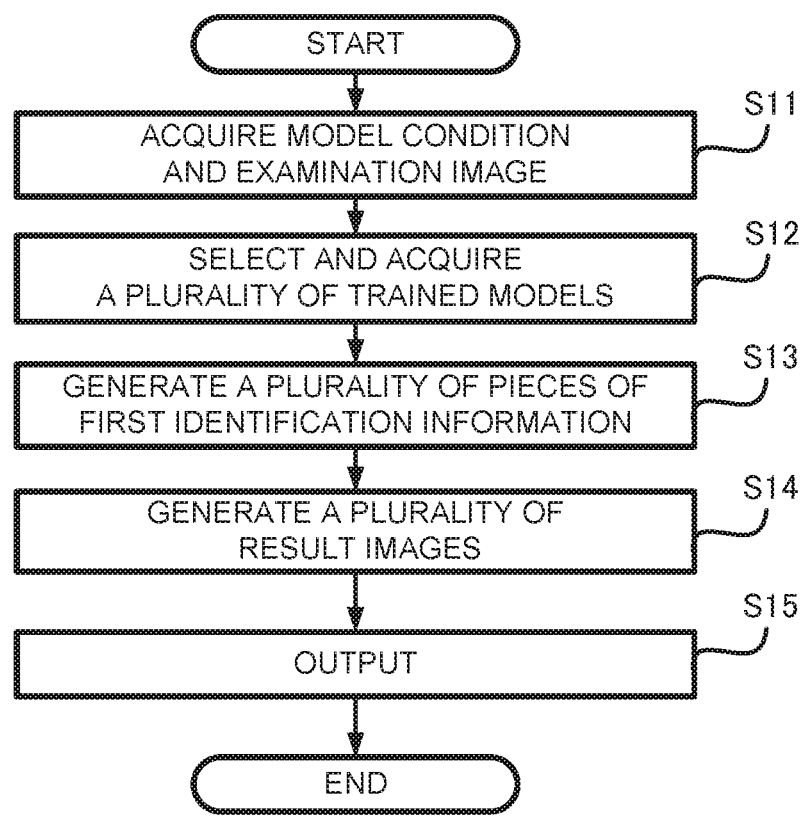
FIG. 7 is a flowchart for an evaluation assistance process in accordance with a first embodiment.
Figure 8:
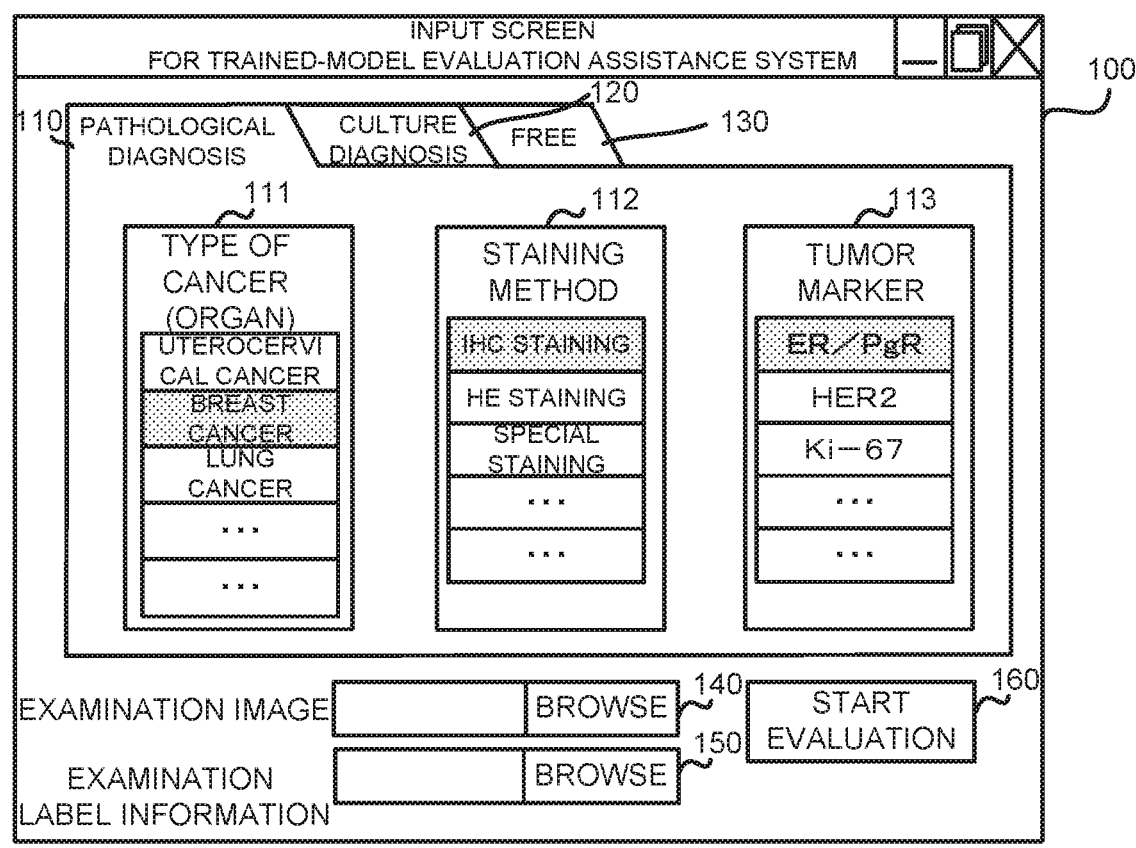
FIG. 8 illustrates an example of an input screen.
Figure 9:
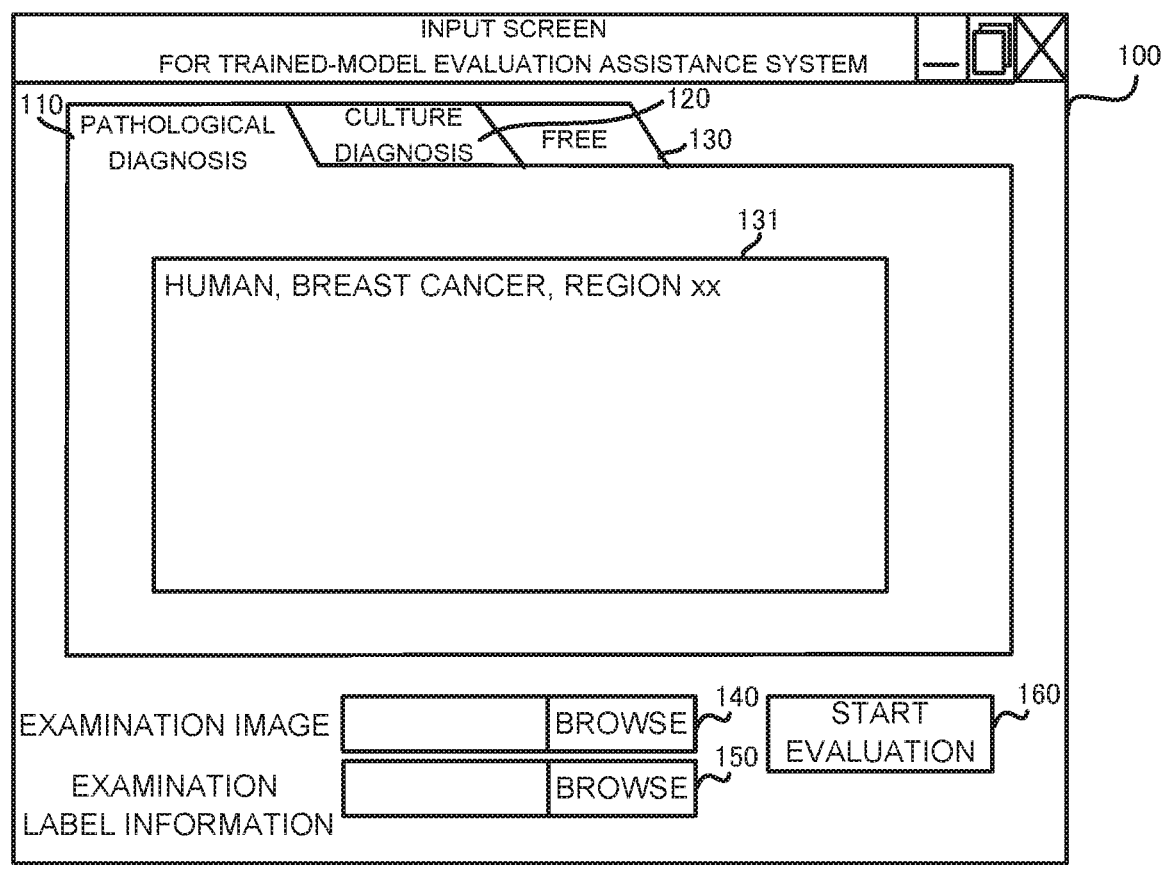
FIG. 9 illustrates another example of an input screen.
Figure 10:
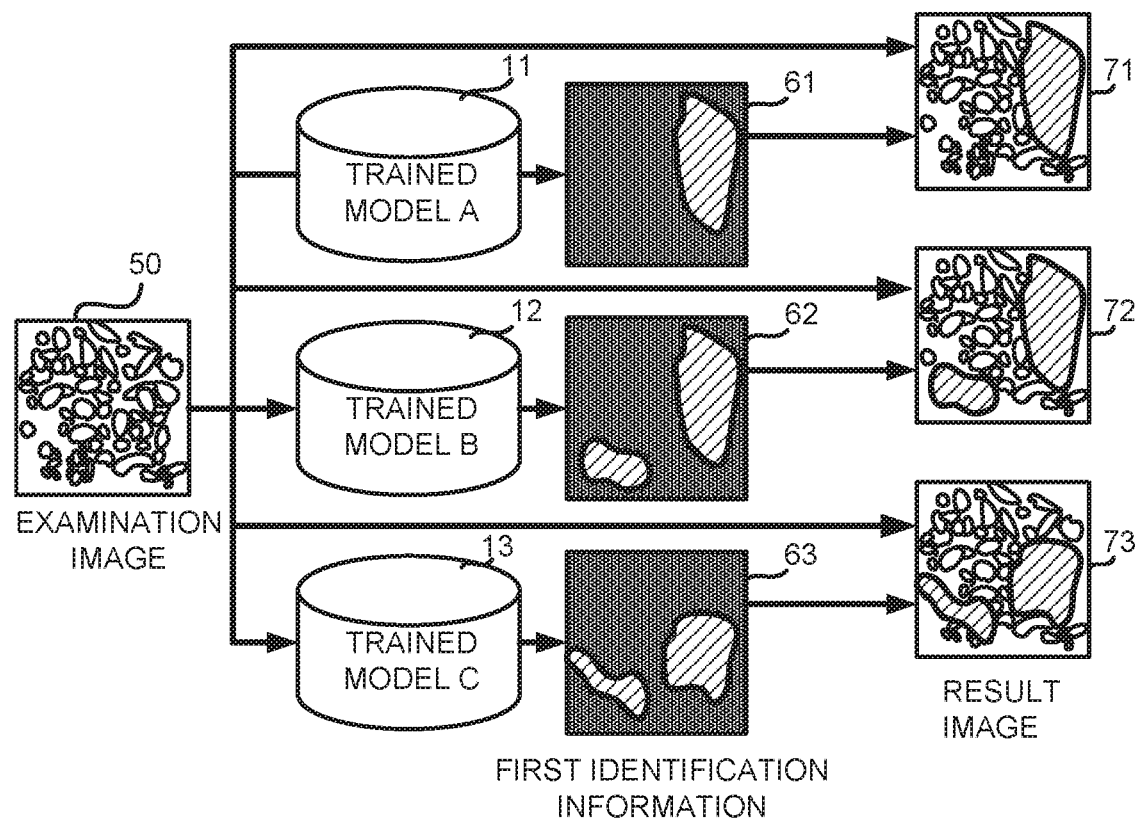
FIG. 10 is an explanatory diagram for a procedure of generating a result image 70.
Figure 11:
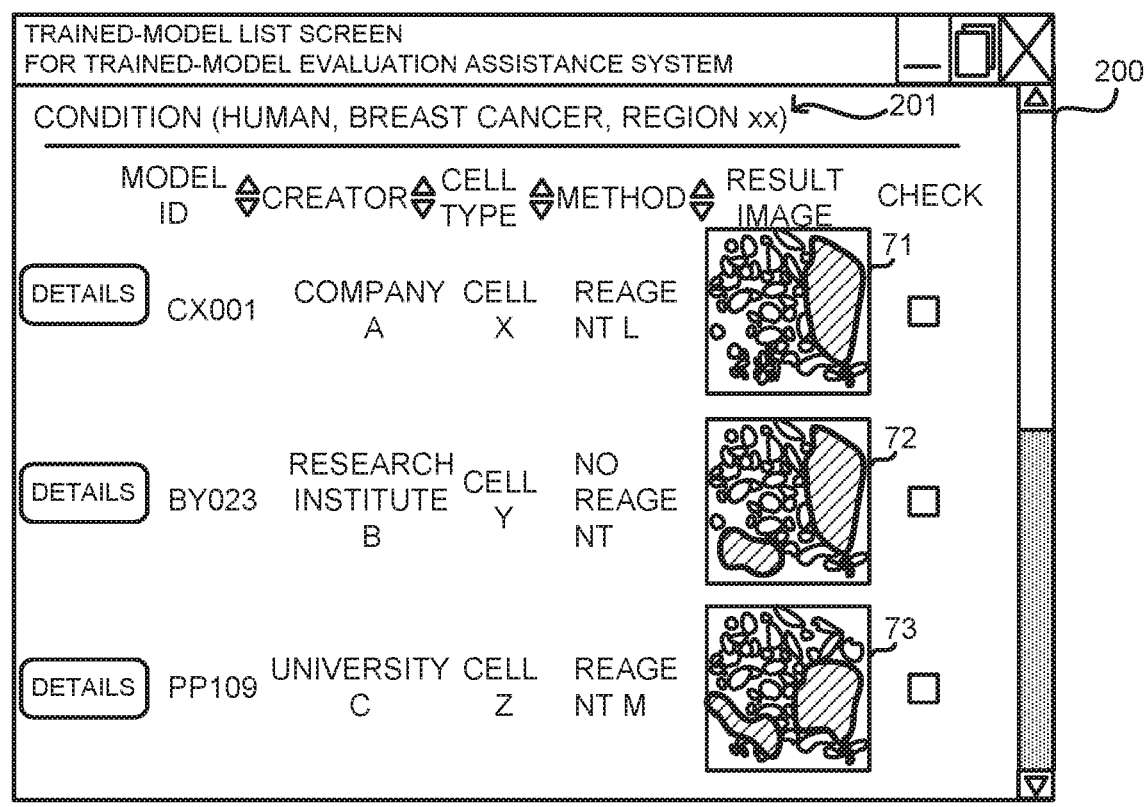
FIG. 11 illustrates an example of a trained model list screen.

FIG. 7 is a flowchart for an evaluation assistance process in accordance with the present embodiment. FIGS. 8 and 9 exemplify an input screen. FIG. 10 is an explanatory diagram for a procedure of generating a result image 70. FIG. 11 illustrates an example of a trained model list screen. The processes depicted in FIG. 7 are performed by, for example, the service providing apparatus 5 executing a predetermined program.

A result image is a result of applying a trained model to an examination image. A result image is also an example of a second image that is a result of processing a first image by a trained model. A result image indicates a result of learning as to which region in an examination image is to be determined as a positive region by a model creator, i.e., indicates a standard for determination by the model creator. When, for example, a trained model that has learned standards for cell detachment determination performed by a certain model creator is used, a positive region in the result image will indicate a region of cells detached from the bottom surface of a container or the like. For a trained model for use in a pathological diagnosis, a positive region will indicate a region determined as a lesioned site by the model creator.

Upon the processes depicted in FIG. 7 being started, the service providing apparatus 5 acquires, from the usage apparatus 6, an examination image 50 and a condition required to be satisfied by a trained model (step S11). In this case, for example, the usage apparatus 6 may access a website provided by the service providing apparatus 5, and in response to this, the service providing apparatus 5 may transmit information on a screen 100 depicted in FIG. 8 to the usage apparatus 6, thereby causing the display apparatus 6*a* of the usage apparatus 6 to display the screen 100. The screen 100 is an input screen for the evaluation assistance system and is used to input an examination image and a condition required to be satisfied by a trained model.

A tab 110 provided on the screen 100 is selected when inputting a condition required to be satisfied by a trained model for use in a pathological diagnosis. A type of cancer, a staining method, and a tumor marker can be respectively specified in regions 111, 112, and 113. A tab 120 is selected when inputting a condition required to be satisfied by a trained model for use in cell culture. A tab 130 is selected when inputting a condition required to be satisfied by a trained model without any constraints. A tab for selecting a diagnostic guideline to be compliant with may also be provided.

FIG. 9 depicts the screen 100 with the tab 130 selected. The following descriptions are given by referring to an example in which to evaluate a trained model appropriate for a human breast cancer test, "HUMAN, BREAST CANCER, REGION xx" is input to a text box 131 as depicted in FIG. 9, an examination image 50 is selected by clicking a button 140, and then a button 160 is clicked. Clicking the button 160 causes the examination image 50 and a condition required to be satisfied by a trained model ("HUMAN, BREAST CANCER, REGION xx") to be uploaded to the service providing apparatus 5. Thus, the service providing apparatus 5 acquires the examination image 50 and the condition required to be satisfied by a trained model. The service providing apparatus 5 may acquire a plurality of examination images 50. Accordingly, step S11 may be an example of the process of acquiring a plurality of first images.

An examination image 50 does not need to be uploaded every time a trained model is searched for, and an image provided in a prior model search process may be reused. For example, an examination image 50 provided in the past may be registered in the service providing apparatus 5, and reference to the registered image (examination image ID) may be specified to read and acquire the image registered in the service providing apparatus 5 as an examination image 50.

Then, the service providing apparatus 5 selects and acquires a plurality of trained models 10 (step S12). In this case, on the basis of the condition acquired in step S11, the service providing apparatus 5 searches metadata 40 registered in advance in the database in association with trained models 10. Then, a plurality of trained models 10 meeting the condition required to be satisfied by a trained model according to the user are extracted. Thus, step S12 is a step of selecting a plurality of trained models 10 from trained models 10 registered in advance, on the basis of the metadata 40 associated with the trained models 10 registered in advance.

Upon acquiring a plurality of trained models 10, the service providing apparatus 5 generates a plurality of pieces of first identification information (step S13). In this case, as depicted in FIG. 10, the service providing apparatus 5 applies the examination image 50 acquired in step S11 to each of the plurality of trained models 10 acquired in step S12 (trained models 11, 12, and 13) so as to generate a plurality of pieces of first identification information (first identification information 61, first identification information 62, first identification information 63). In this example, each of the plurality of pieces of first identification information is information identifying a region predicted to be a positive region by a corresponding trained model 10.

As many pieces of first identification information as the number of examination images 50 are generated for each of the trained models acquired in step S12. Accordingly, although FIG. 10 depicts an example in which one piece of first identification information is generated for each trained model, a plurality of pieces of first identification information are generated for each trained model when a plurality of examination images 50 are acquired in step S11.

Then, the service providing apparatus 5 generates a plurality of result images (step S14). In this case, as depicted in FIG. 10, the service providing apparatus 5 superimposes each of the plurality of pieces of first identification information generated in step S13 onto the examination image 50 acquired in step S11, thereby generating a plurality of result images (result images 71, 72, and 73). Accordingly, step S14 is an example of the process of generating a plurality of second images. When a plurality of first images are acquired in step S11, step S14 is an example of the process of generating a plurality of second images for each of the plurality of first images.

Finally, the service providing apparatus 5 outputs the plurality of result images (step S15). In this case, the service providing apparatus 5 outputs each of the plurality of result images generated in step S14 after associating the result image with a corresponding trained model 10 of the plurality of trained models 10 selected in step S12. In particular, the service providing apparatus 5 transmits a screen 200 depicted in FIG. 11 to the usage apparatus 6 so as to cause the display apparatus 6a of the usage apparatus 6 to display the screen 200. The screen 200 is a trained model list screen for the evaluation assistance system and displays a plurality of result images generated using a plurality of trained models 10 in a manner such that the result images are arranged in order.

The screen 200 depicted in FIG. 11 displays, below a model condition field 201, combinations of pieces of identification information (model IDs) of trained models, pieces of metadata (creator, cell type, method), and result images which are arranged in order, the number of combinations being equal to the number of trained models selected in step S12. Thus, step S15 is an example of the process of displaying each of the plurality of trained models in association with a corresponding second image of the plurality of second images. When a plurality of first images are acquired in step S11, step S15 is an example of the process of displaying each of a plurality of trained models in association with at least one corresponding second image of a plurality of second images and includes a process of selecting at least one second image from the plurality of second images for each of the plurality of first images. Meanwhile, since the combinations include metadata, step S15 is also an example of the process of displaying each of a plurality of trained models in association with at least one corresponding second image of a plurality of second images and metadata associated with a corresponding trained model of a plurality of trained models.

An order in which the combinations are arranged may be decided on the basis of the degree of conformity to a condition that the user of the trained model requires to be satisfied. For example, when a certain culture condition is specified, trained models trained using images of cells cultured under a culture condition closer to the specified culture condition may be arranged in a prioritized manner. Accordingly, step S15 may include a process of assigning priority levels to a plurality of combinations on the basis of a plurality of pieces of metadata associated with a plurality of trained models and also a process of displaying the plurality of combinations in an order of arrangement compliant with the priority levels. Note that each of the plurality of combinations is a combination of a trained model, at least one second image, and meta data which correspond to each other. A sort button provided on the screen 200 may be clicked to change the order of arrangement in accordance with a condition prioritized by the user.

As described above, the system 1 can perform the evaluation assistance process in accordance with the present embodiment such that results of image recognition implemented for an examination image by a plurality of trained models are output as a plurality of result images, thereby allowing the user to easily compare the plurality of result images. An examination image is an image specified by the user. A good recognition result indicated by a result image obtained by inputting an examination image strongly suggests high performance to be attained when the user uses a trained model for his/her own purpose. Accordingly, while comparing a plurality of result images generated on the basis of an examination image, the user checks the difference between a recognition result indicated by each result image and a recognition result compliant with his/her standards for evaluation. Thus, the user can grasp the goodness of fit of each trained model to the user's purpose. Hence, a trained model fitting the user's purpose can be easily specified. Accordingly, the evaluation assistance method in accordance with the present embodiment can assist the user evaluating, according to the user's standard, trained models built by others.

FIG. 11 depicts an example in which a plurality of trained models are each displayed in association with at least one corresponding second image, but a first image may also be displayed. Thus, in step S15, a plurality of trained models may each be displayed in association with at least one second image corresponding to the trained model and at least one first image corresponding to the at least one second image. Displaying the first image together with the second image allows the second image to be evaluated more properly, with the result that the trained model can be evaluated more properly.

FIG. 11 depicts an example in which a plurality of trained models are each displayed in association with at least one corresponding second image, but the reliability of the second image may also be displayed. Thus, in step S15, a plurality of trained models may each be displayed in association with at least one second image corresponding to the trained model and the reliability of the at least one second image. A reliability is the reliability of a result image generated by a trained model, more specifically the reliability of first identification information output when the trained model generates a result image. In particular, a reliability indicates a degree of certainty with which a trained model has generated first identification information. Displaying the reliability together with the second image allows the trained model to be evaluated more properly.

When displaying reliabilities, the service providing apparatus 5 may assign priority levels to a plurality of combinations on the basis of the reliabilities of a plurality of second images and may also display the plurality of combinations in an order of arrangement compliant with the priority levels. Note that each of the plurality of combinations is a combination of a trained model, at least one second image, and the reliability of the at least one second image which correspond to each other. Higher priority levels may be assigned for a higher reliability. Alternatively, higher priority levels may be assigned for a lower reliability. Assigning higher priority levels for a lower reliability can reduce the likelihood of the performance of trained models being overestimated. In the meantime, reliabilities may be used only for assignment of priority levels without being displayed.

Second Embodiment

Figure 12:
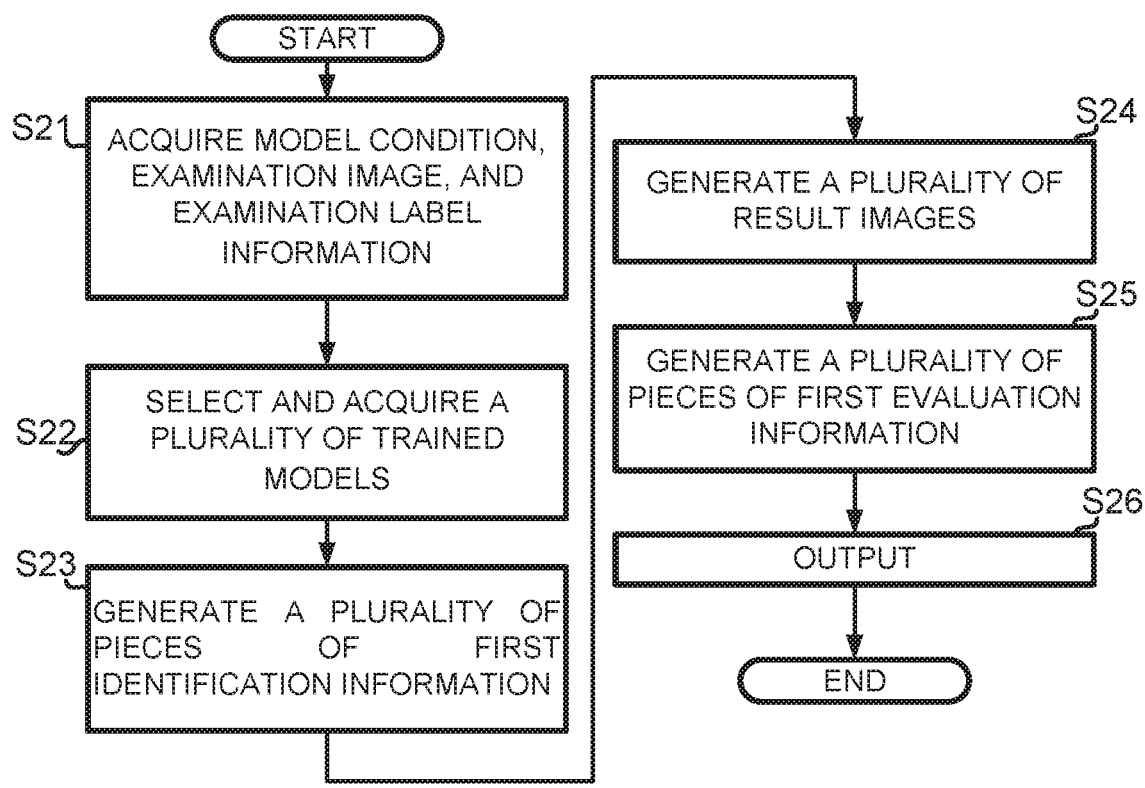
FIG. 12 is a flowchart for an evaluation assistance process in accordance with a second embodiment.
Figure 13:
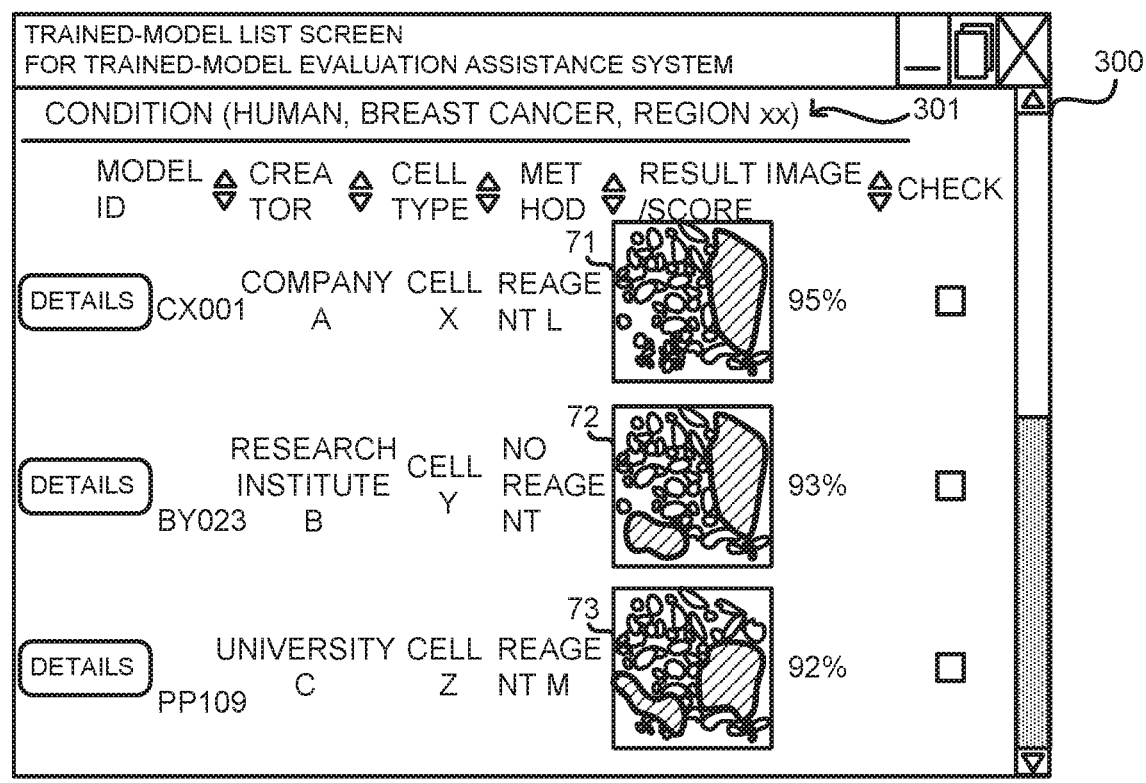
FIG. 13 illustrates another example of a trained model list screen.

FIG. 12 is a flowchart for an evaluation assistance process in accordance with the present embodiment. FIG. 13 illustrates another example of a trained model list screen. The processes depicted in FIG. 12 are performed by, for example, the service providing apparatus 5 executing a predetermined program.

Upon the processes depicted in FIG. 12 being started, the service providing apparatus 5 acquires, from the usage apparatus 6, an examination image 50, examination label information, and a condition required to be satisfied by a trained model (step S21). The process of step S21 is different from the process of step S11 in FIG. 7 in terms of the acquiring of examination label information but is similar to the process of step S11 in terms of the acquiring of an examination image 50 and a condition required to be satisfied by a trained model.

Examination label information is an example of first label information indicating a desired result of the processing of a first image. For example, examination label information may identify a correct answer region that is a positive or negative region included in the examination image 50. Examination label information can be specified by clicking a button 150 on the screen 100 depicted in FIG. 9 and uploaded to the service providing apparatus 5 together with, for example, the examination image 50 and the condition required to be satisfied by a trained model ("HUMAN, BREAST CANCER, REGION xx"). Thus, the service providing apparatus 5 acquires the examination image 50, examination label information, and the condition required to be satisfied by a trained model. In step S21, when a plurality of first images are acquired, a plurality of pieces of first label information corresponding to the plurality of first images are acquired.

Examination label information does not need to be uploaded every time a trained model is searched for, and examination label information provided in a prior model search process may be reused. For example, examination label information provided in the past may be registered in the service providing apparatus 5, and reference to the registered information (examination label information ID) may be specified to read and acquire the examination label information registered in the service providing apparatus 5.

Then, the service providing apparatus 5 acquires a plurality of trained models 10 (step S22), generates a plurality of pieces of first identification information (step S23), and generates a plurality of result images (step S24). In particular, first identification information and a result image are generated for each of the trained models. Note that the processes of steps S22-S24 are similar to those of steps S12-S14 depicted in FIG. 7.

In addition, the service providing apparatus 5 generates a plurality of pieces of first evaluation information (step S25). Each of the plurality of pieces of first evaluation information is generated on the basis of each of the plurality of pieces of first identification information generated in step S23 and the examination label information acquired in step S21. Thus, the service providing apparatus 5 generates first evaluation information for each of the trained models. Step S25 is an example of the process of generating a plurality of pieces of first evaluation information corresponding to a plurality of second images. Note that when a plurality of first images and a plurality of pieces of first label information have been acquired in step S21, a plurality of pieces of first evaluation information are generated on the basis of a plurality of second images and the plurality of pieces of first label information.

First evaluation information is obtained by quantitatively evaluating a trained model 10 on the basis of examination label information and is, for example, a precision, a recall, or a F-measure which is a harmonic mean between the precision and the recall. Alternatively, first evaluation information may be a specificity or an accuracy. First evaluation information indicating a higher value is not necessarily more preferable. For example, first evaluation information may be a false negative rate or a false positive rate. First evaluation information is not limited to a single indicator and may be an arbitrary combination of the plurality of indicators described above.

In step S25, the service providing apparatus 5 specifies regions corresponding to true positive, false positive, false negative, or true negative by comparing pieces of examination label information and pieces of first identification information, both specifying regions on an image. Upon these regions being specified, the service providing apparatus 5 calculates first evaluation information using the areas of these regions.

There may be one or more examination images. When there are a plurality of examination images, in addition to the values of a plurality of pieces of first evaluation information calculated from a plurality of pieces of examination label information corresponding to the examination images, a representative value may be calculated for the plurality of pieces of first evaluation information. For example, the representative value may be an average or a median.

Finally, the service providing apparatus 5 outputs the plurality of result images and the plurality of pieces of first evaluation information (step S26). In this case, the service providing apparatus 5 outputs each of the plurality of result images generated in step S24 after associating the result image with a corresponding trained model 10 of the plurality of trained models 10 selected in step S22 and a piece of corresponding first evaluation information of the plurality of pieces of first evaluation information generated in step S25. In particular, the service providing apparatus 5 transmits a screen 300 depicted in FIG. 13 to the usage apparatus 6 so as to cause the display apparatus 6a of the usage apparatus 6 to display the screen 300. The screen 300 is a trained model list screen for the evaluation assistance system and displays a plurality of result images generated using a plurality of trained models 10 and a plurality of pieces of first evaluation information associated with the plurality of result images, in a manner such that the result images and the plurality of pieces of first evaluation information are arranged in order.

When a plurality of examination images are acquired in step S21, a plurality of result images are generated for each of the plurality of trained models 10. In this situation, one or more result images may be displayed for each of the trained models 10. For each of the plurality of trained models, one or more result images to be displayed may be selected on the basis of a plurality of pieces of first evaluation information calculated from the plurality of examination images and the representative value of the plurality of pieces of first evaluation information. For example, the highest, or the highest and one or more subsequent values, among F-measures calculated for the examination images may be selected, and one or more result images corresponding to the selected one or more F-measures may be selected. Alternatively, for example, one or more result images corresponding to a piece of first evaluation information that is the closest to the representative value of the plurality of pieces of first evaluation information may be selected and displayed. A plurality of result images may be displayed for each of the trained models in a manner such that the plurality of result images are displayed by being arranged in order in, for example, each of the areas depicted in FIG. 13 in which result images are displayed. A slider bar may be displayed below the images so that only an image specified by the user among a plurality of result images can be selectively displayed.

The screen 300 depicted in FIG. 13 displays, below a model condition field 301, combinations of pieces of identification information (model ID) of trained models, pieces of metadata (creator, cell type, method), result images, and pieces of first evaluation information (scores) which are arranged in order, the number of combinations being equal to the number of trained models selected in step S22. Thus, step S26 is an example of the process of displaying each of a plurality of trained models in association with at least one second image and at least one piece of first evaluation information corresponding to the at least one second image among a plurality of pieces of first evaluation information.

Step S26 may include a process of assigning priority levels to the plurality of combinations on the basis of the plurality of pieces of first evaluation information. Each of the plurality of result images may be output in accordance with the priority level after being associated with both a corresponding trained model and a corresponding first evaluation information. Thus, an order in which the combinations are arranged on the screen 300 may be decided on in accordance with the assigned priority levels, and the plurality of combinations may be displayed in an order of arrangement compliant with the priority levels. A sort button provided on the screen 300 may be clicked to change the order of arrangement in accordance with a condition prioritized by the user.

For example, when first evaluation information indicating a higher value is an indicator of a more preferable result, e.g., when first evaluation information is a F-measure, the service providing apparatus 5 may assign higher priority levels to combinations that include first evaluation information indicating a higher value. When first evaluation information indicating a lower value is an indicator of a more preferable result, the service providing apparatus 5 may assign higher priority levels to combinations that include first evaluation information indicating a lower value. Note that FIG. 13 depicts an example in which the displaying of trained models with first evaluation information indicating a high value is prioritized.

In addition, when a plurality of examination images are acquired and first evaluation information indicating a higher value is an indicator of a more preferable result, the service providing apparatus 5 may select, for each of a plurality of trained models, one or more result images corresponding to first evaluation information indicating a high value. When a plurality of examination images are acquired and first evaluation information indicating a lower value is an indicator of a more preferable result, the service providing apparatus 5 may select, for each of a plurality of trained models, one or more result images corresponding to first evaluation information indicating a low value. A selection standard for result images may be linked to a sort button provided on the screen 300.

The service providing apparatus 5 may assign priority levels to a plurality of combinations on the basis of the frequencies of use of a plurality of trained models and in addition, may display the plurality of combinations in an order of arrangement compliant with the priority levels. Note that each of the plurality of combinations is a combination of a trained model, at least one second image, and at least one piece of first evaluation information which correspond to each other. For example, the number of times the model providing request in S6 in FIG. 3 has been made may be used as a substitute for the frequency of use.

When the system 1 performs the evaluation assistance process in accordance with the present embodiment, a plurality of result images are output as in the first embodiment. Accordingly, the user can check the difference between a recognition result indicated by each result image and a recognition result compliant with his/her standards for evaluation, so that the user can grasp the goodness of fit of each trained model to the user's purpose.

In the present embodiment, in addition, a plurality of pieces of first evaluation information are output together with a plurality of result images. Thus, using the plurality of pieces of first evaluation information, a plurality of trained models can be quantitatively compared and evaluated. Examination label information is information on a region determined as a correct answer by the user in accordance with his/her standards for evaluation. Hence, first evaluation information obtained by evaluating a trained model on the basis of examination label information is considered to have a strong correlation with the performance of the trained model when being used for the user's purpose. Accordingly, the present embodiment allows a trained model fitting the user's purpose to be more easily specified than the first embodiment. Moreover, outputting a plurality of result images in accordance with priority levels based on first evaluation information allows for a reduction in time required to specify a trained model fitting the user's purpose. Therefore, the evaluation assistance method in accordance with the present embodiment can also assist the user evaluating, according to the user's standard, a trained model built by others.

Third Embodiment

Figure 14:
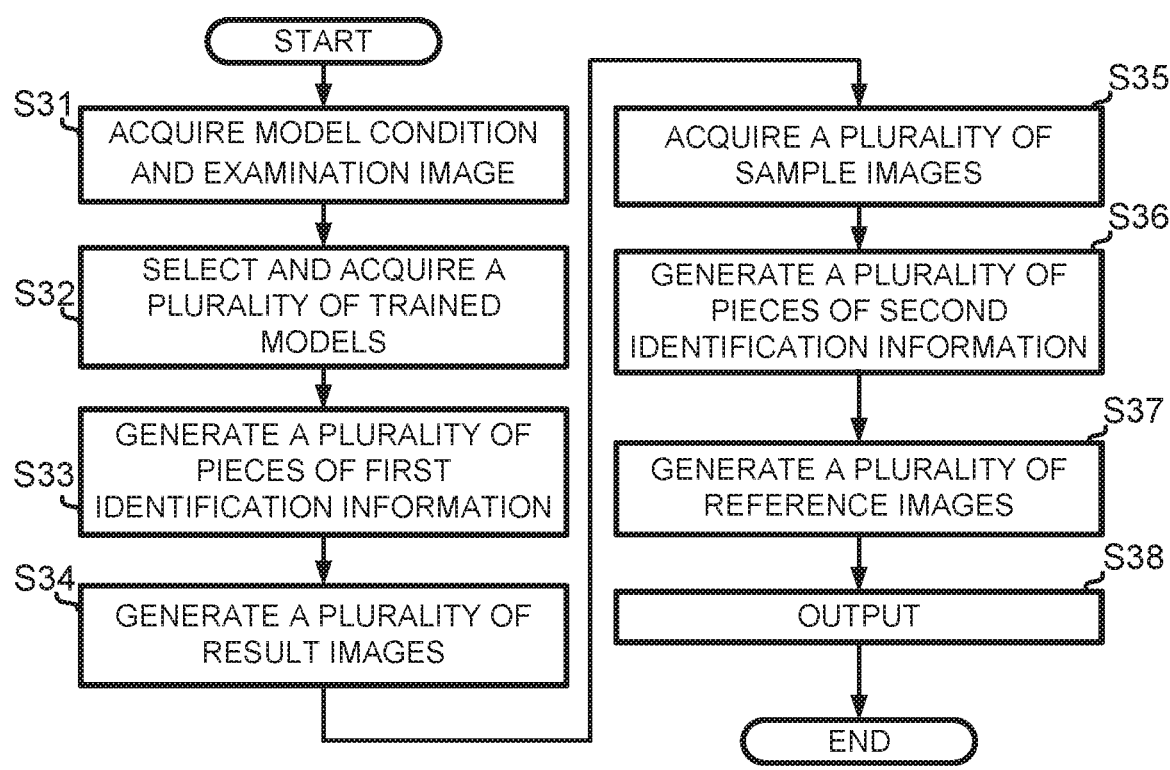
FIG. 14 is a flowchart for an evaluation assistance process in accordance with a third embodiment.
Figure 15:
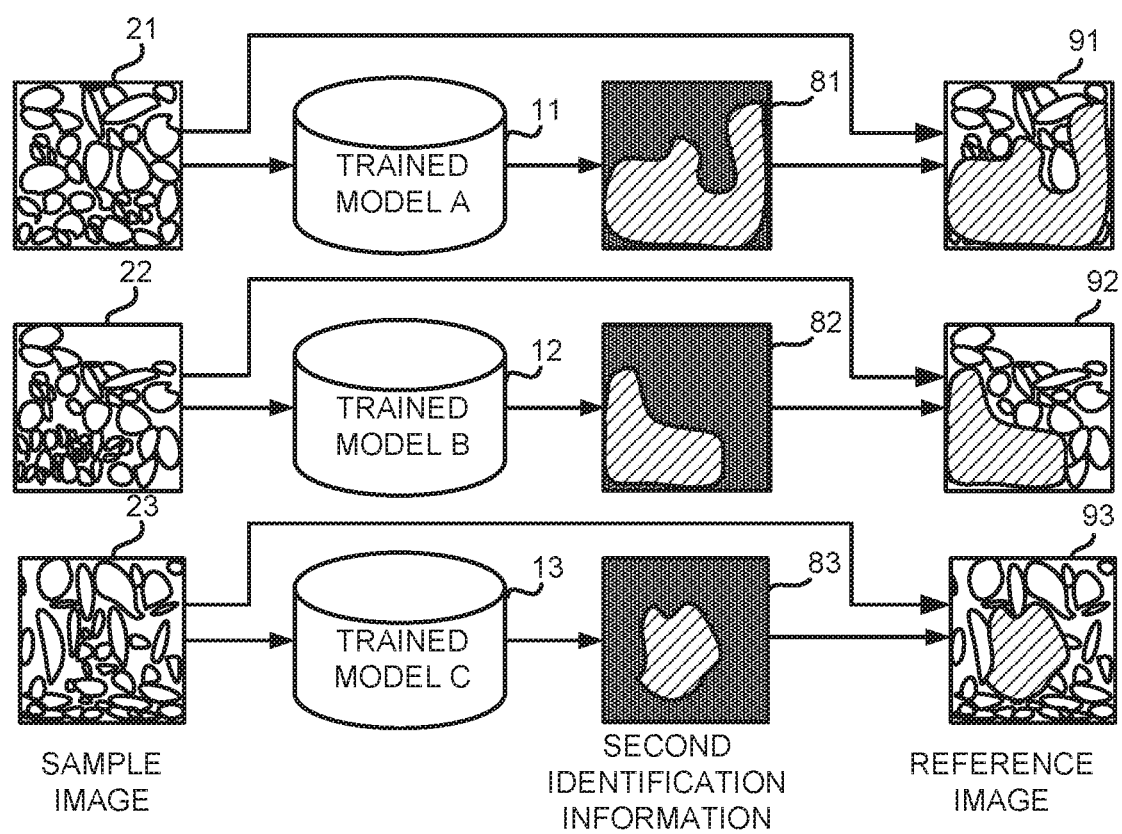
FIG. 15 is an explanatory diagram for a procedure of generating a reference image 90.
Figure 16:
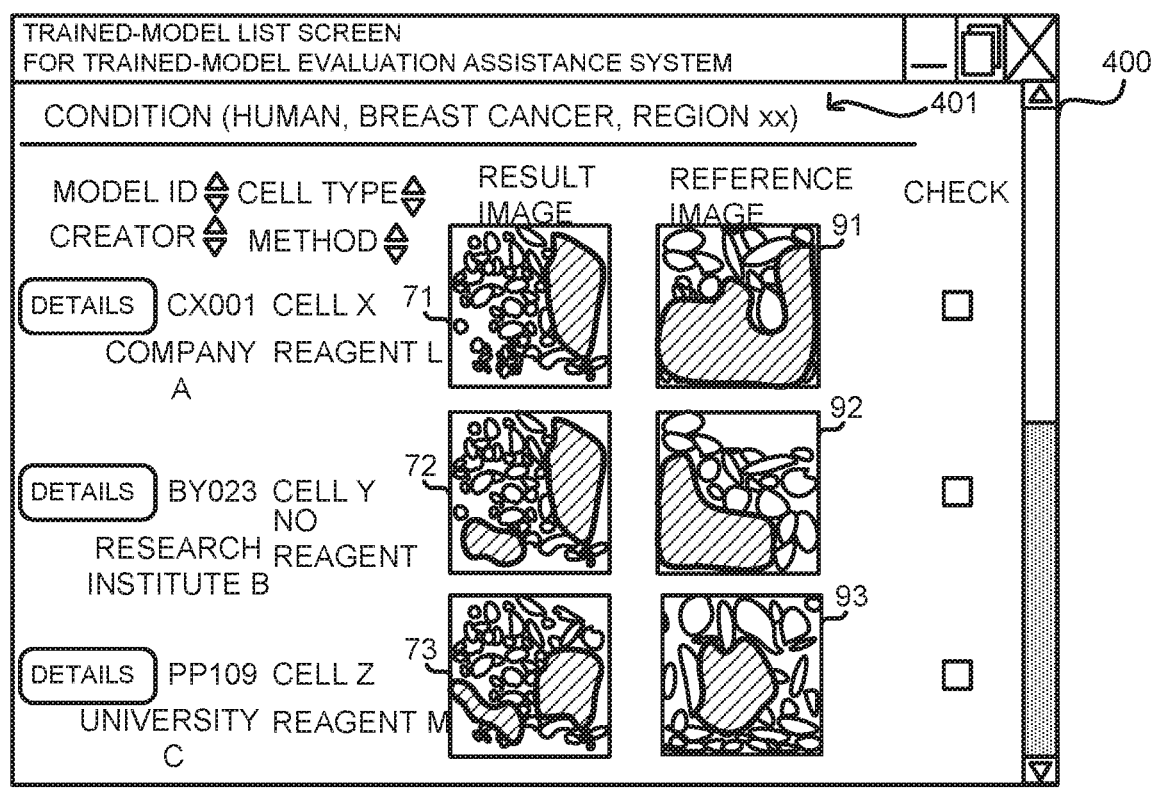
FIG. 16 illustrates still another example of a trained model list screen.
Figure 17:
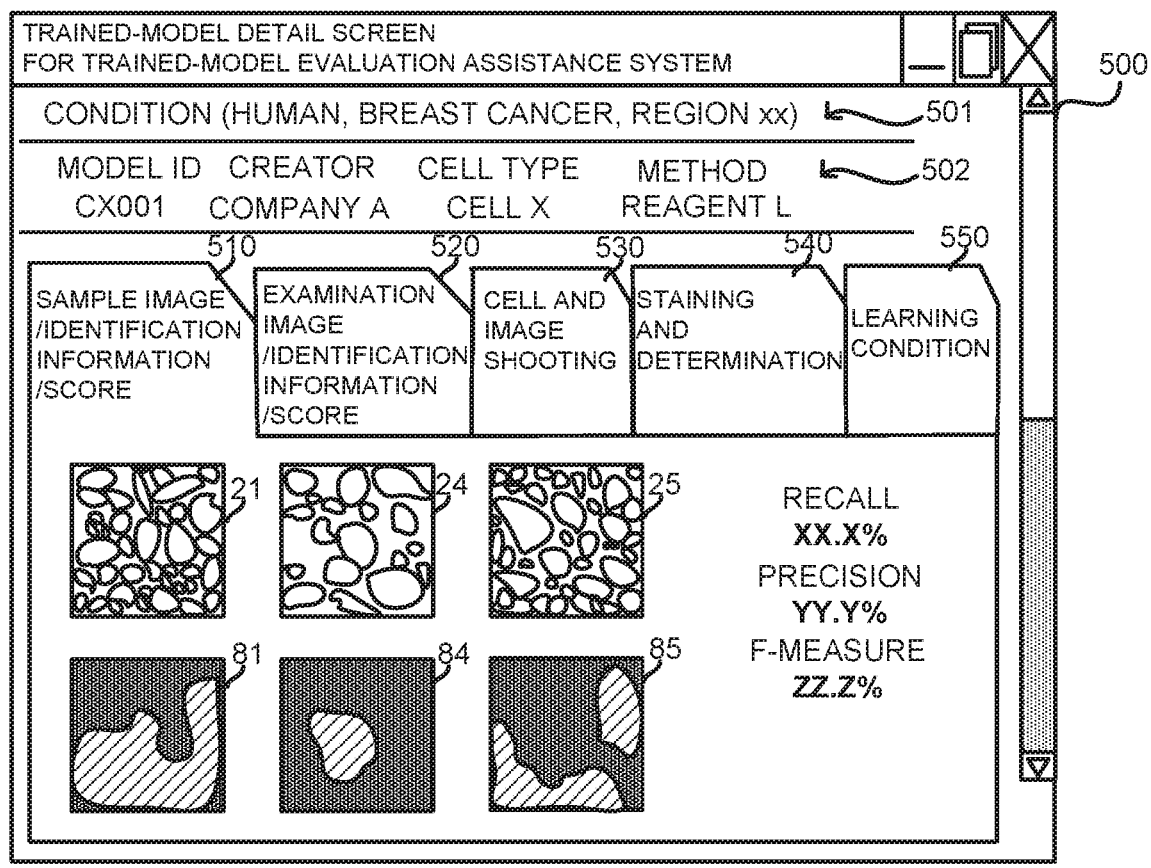
FIG. 17 illustrates an example of a trained model detail screen.

FIG. 14 is a flowchart for an evaluation assistance process in accordance with the present embodiment. FIG. 15 is an explanatory diagram for a procedure of generating a reference image 90. FIG. 16 illustrates a further example of a trained model list screen. FIG. 17 illustrates an example of a trained model detail screen. The processes depicted in FIG. 14 are performed by, for example, the service providing apparatus 5 executing a predetermined program.

Upon the processes depicted in FIG. 14 being started, the service providing apparatus 5 acquires, from the usage apparatus 6, an examination image 50 and a condition required to be satisfied by a trained model (step S31). Then, the service providing apparatus 5 acquires a plurality of trained models (step S32), generates a plurality of pieces of first identification information (step S33), and generates a plurality of result images (step S34). In particular, first identification information and a result image are generated for each of the trained models. Note that the processes of steps S31-S34 are similar to those of steps S11-S14 depicted in FIG. 7.

In addition, the service providing apparatus 5 acquires a plurality of sample images (step S35). The plurality of sample images are each an example of a third image used in a training process for a corresponding trained model of the plurality of trained models acquired in step S32. Accordingly, step S35 is an example of the process of acquiring a plurality of third images. Sample images are registered in the database in advance together with trained models. In step S35, at least one sample image may be acquired for each trained model, or a plurality of sample images may be acquired for each trained model. The following descriptions are given with reference to an example in which one sample image is acquired for each trained model.

Upon acquiring a plurality of sample images, the service providing apparatus 5 generates a plurality of pieces of second identification information (step S36). In this case, as depicted in FIG. 15, the service providing apparatus 5 applies, to each of the plurality of trained models 10 acquired in step S32 (trained models 11, 12, and 13), a corresponding sample image of the plurality of sample images acquired in step S35 (sample images 21, 22, and 23) so as to generate a plurality of pieces of second identification information (second identification information 81, second identification information 82, second identification information 83). In this example, each of the plurality of pieces of second identification information identifies a region predicted to be a positive region by a corresponding trained model 10. Note that as many pieces of second identification information as the number of sample images are generated.

Then, the service providing apparatus 5 generates a plurality of reference images (step S37). The plurality of reference images are each an example of a fourth image that is a result of processing a corresponding third image of the plurality of third images by a corresponding trained model of the plurality of trained models. Accordingly, step S37 is an example of the process of generating a plurality of fourth images. In this case, as depicted in FIG. 15, the service providing apparatus 5 superimposes each of the plurality of pieces of second identification information generated in step S36 onto a corresponding sample image of the sample images acquired in step S35, thereby generating a plurality of reference images (reference images 91, 92, and 93).

Finally, the service providing apparatus 5 outputs the plurality of result images and the plurality of reference images (step S38). In this case, the service providing apparatus 5 outputs each of the plurality of result images generated in step S34 after associating the result image with a corresponding trained model 10 of the plurality of trained models 10 selected in step S32 and a corresponding reference image of the plurality of reference images generated in step S37. In particular, the service providing apparatus 5 transmits a screen 400 depicted in FIG. 16 to the usage apparatus 6 so as to cause the display apparatus 6a of the usage apparatus 6 to display the screen 400. The screen 400 is a trained model list screen for the evaluation assistance system and displays a plurality of result images and a plurality of reference images generated using a plurality of trained models 10 in a manner such that the these images are arranged in order.

The screen 400 depicted in FIG. 16 displays, below a model condition field 401, combinations of pieces of identification information (model IDs) of trained models, pieces of metadata (creator, cell type, method), result images, and reference images which are arranged in order, the number of combinations being equal to the number of trained models selected in step S32. Thus, step S38 is an example of the process of displaying each of the plurality of trained models in association with a corresponding second image of the plurality of second images and a corresponding fourth image of the plurality of fourth images. An order in which the combinations are arranged may be decided on the basis of the degree of conformity to a condition that the user of the trained model requires to be satisfied. A sort button provided on the screen 400 may be clicked to change the order of arrangement in accordance with a condition prioritized by the user.

When the system 1 performs the evaluation assistance process in accordance with the present embodiment, a plurality of result images are output as in the first embodiment. Accordingly, the user can check the difference between a recognition result indicated by each result image and a recognition result compliant with his/her standards for evaluation, so that the user can grasp the goodness of fit of each trained model to the user's purpose.

In the present embodiment, in addition, a plurality of reference images are output together with a plurality of result images. The plurality of reference images are sample images with second identification information superimposed thereon. Since a sample image is selected by a model provider, the user can grasp, by checking a reference image, a sample for which the model provider intended to build a trained model. In addition, second identification information is a result of output of a trained model trained using information on a region determined by the model provider as a correct answer in accordance with his/her standards for evaluation, so that the user can grasp, by checking a reference image, the standards for determination with which the model provider trained the trained model. Accordingly, the user can grasp the intention of the model provider by checking a reference image, so that the reference image can be used as information for predicting the goodness of fit of the trained model to the user's purpose. Thus, the present embodiment allows a trained model that generated a result image indicating a result close to the user's recognition by chance to be prevented from being selected. Therefore, a trained model fitting the user's purpose can be specified more accurately than in the first embodiment.

The sample images acquired in step S35 in the present embodiment are desirably validation images. This is because acquiring validation images as sample images allows the performances of trained models to be more fairly evaluated in comparison to when acquiring training images.

Although the present embodiment has been described by referring to an example in which second identification information is generated in step S36, second identification information generated in advance may be acquired in step S36. This is because second identification information can be generated from a trained model and a sample image registered in the database, before a request from the user is input to the service providing apparatus 5. Second identification information may be generated when the service providing apparatus 5 accepts a model or at any timing after the model acceptance. Second identification information may be generated by the model providing apparatus, rather than by the service providing apparatus 5, and may be uploaded to the service providing apparatus 5 together with a trained model and the like when providing a model. Using second identification information generated in advance allows a request from the user to be responded to more rapidly.

In the present embodiment, a "details" button provided on the screen 400 may be clicked to output, for example, a screen 500 depicted in FIG. 17 from the service providing apparatus 5. The screen 500 is a trained model detail screen for the evaluation assistance system and displays more specific information pertaining to a selected trained model 10.

The screen 500 depicted in FIG. 17 is provided with a plurality of tabs (tabs 510, 520, 530, 540, and 550) below a model condition field 501 and a model information field 502. FIG. 17 depicts a situation in which the tab 510 has been selected. In particular, a plurality of sample images used to build a trained model (sample images 21, 24, and 25) and a plurality of pieces of corresponding second identification information (second identification information 81, second identification information 84, second identification information 85) are displayed. In addition, main evaluation indicators such as a recall, a precision, and a F-measure are also displayed as second evaluation information. By referring to such images and information, the user can better grasp the intention of the model provider.

Selecting the tab 520 displays various information that would be obtained by applying examination images to a trained model. Selecting the tab 530 displays details of cell information and image shooting information. Selecting the tab 540 displays details of staining information and determination conditions. Selecting the tab 550 displays details of learning conditions.

Fourth Embodiment

Figure 18:
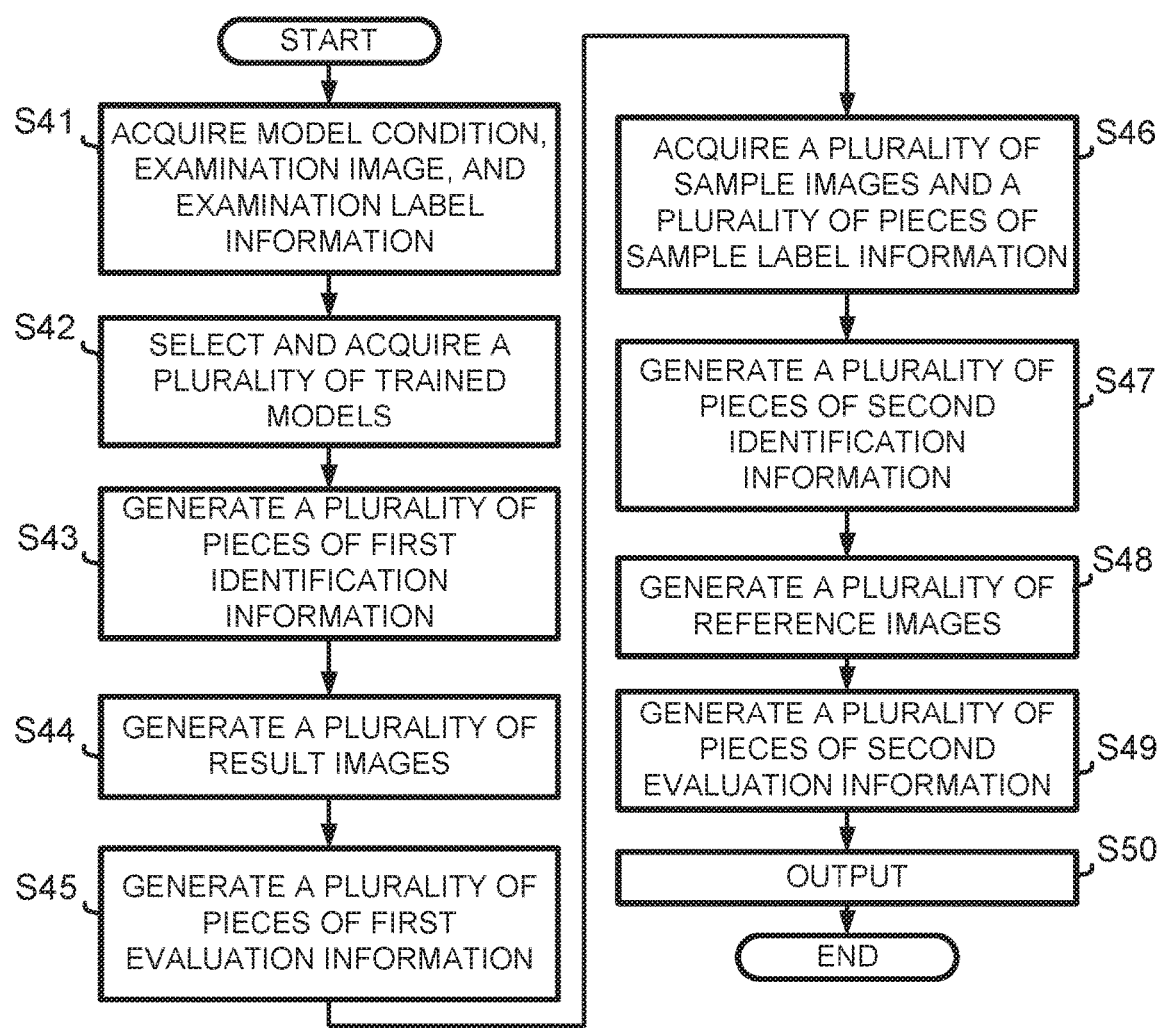
FIG. 18 is a flowchart for an evaluation assistance process in accordance with a fourth embodiment.
Figure 19:
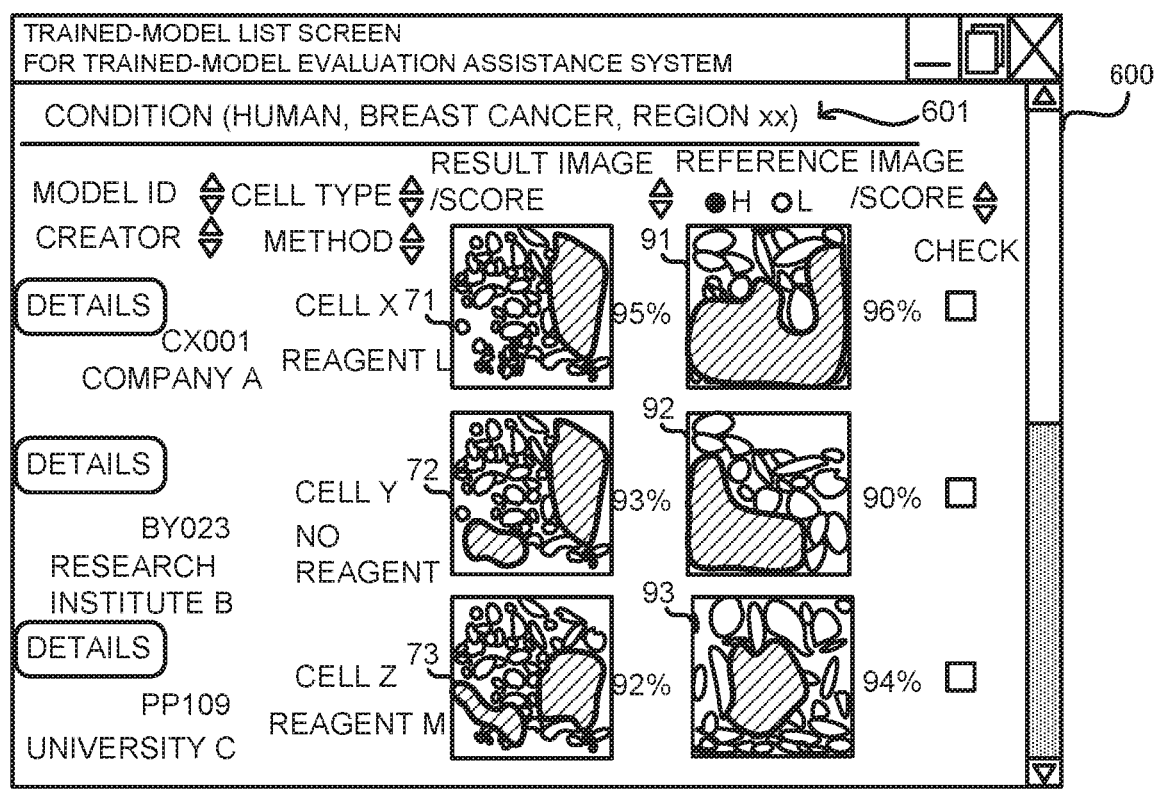
FIG. 19 illustrates yet another example of a trained model list screen.
Figure 20:
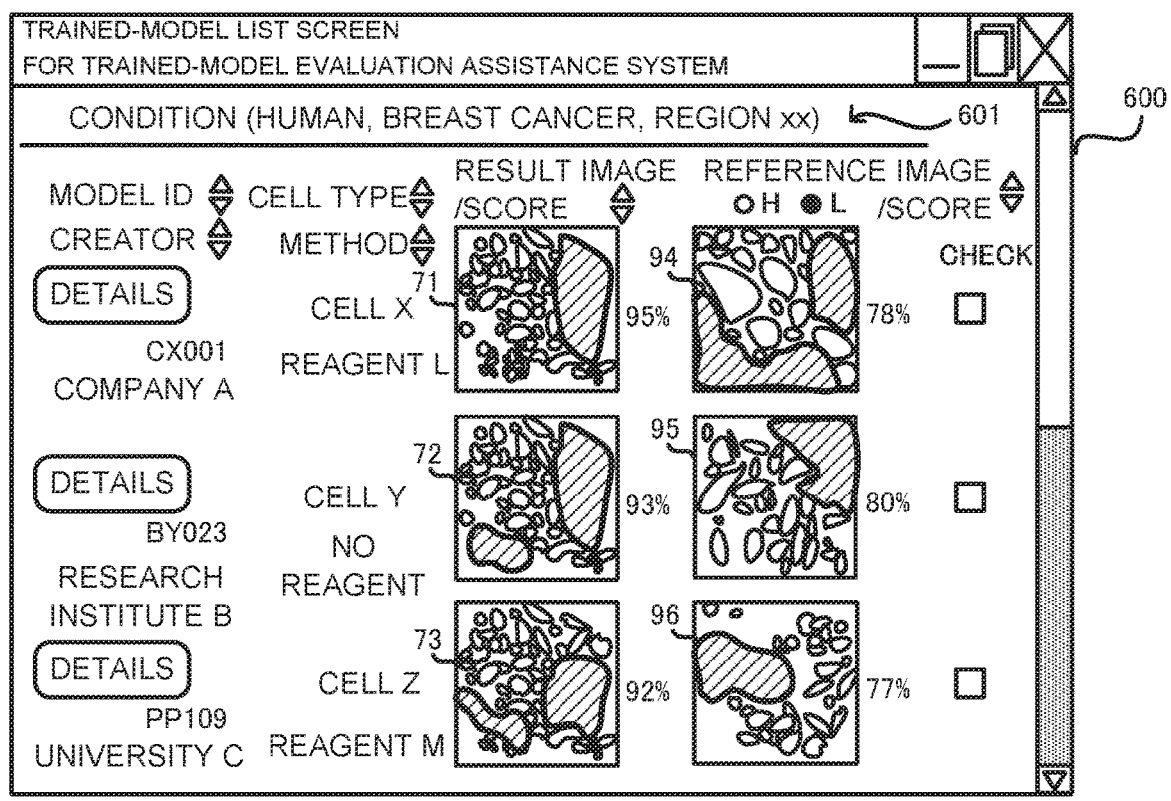
FIG. 20 illustrates a further example of a trained model list screen.
Figure 21:
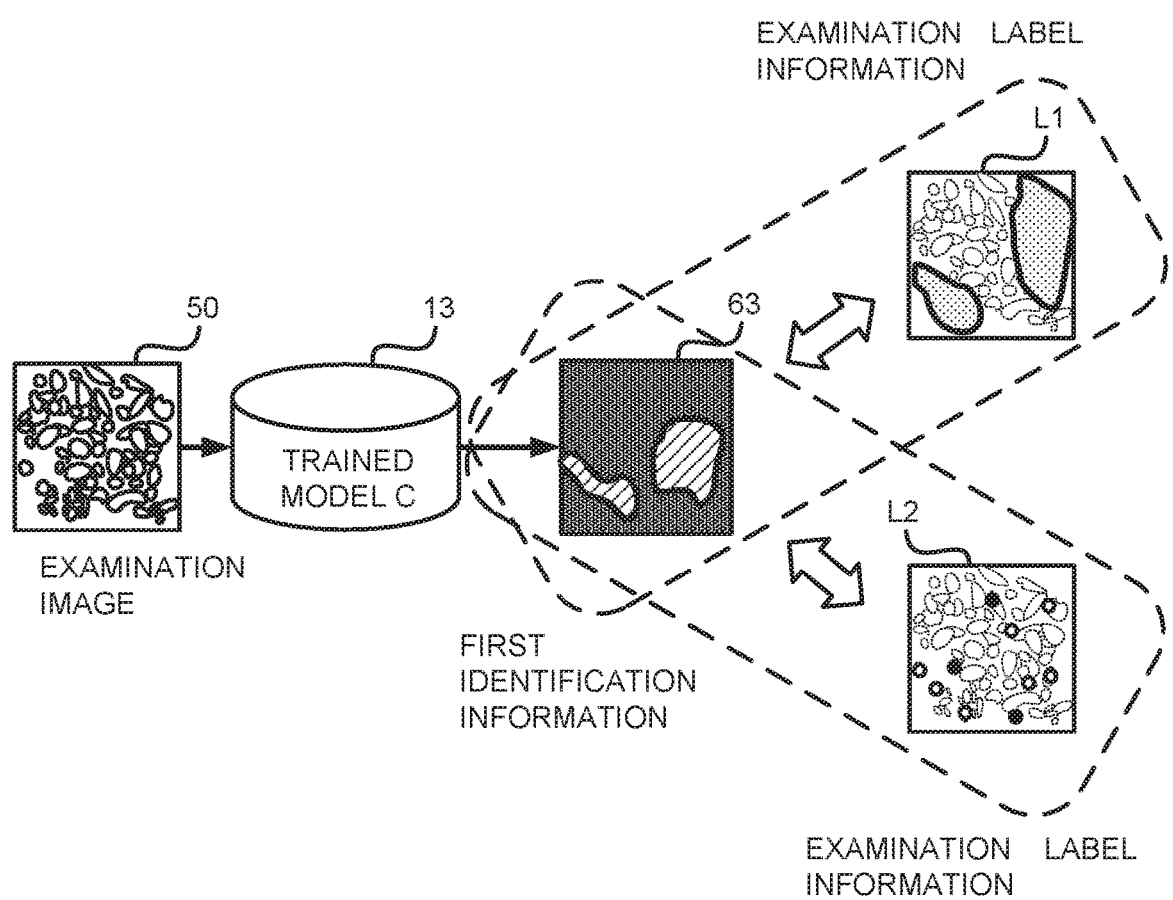
FIG. 21 is an explanatory diagram for a method of generating evaluation information.

FIG. 18 is a flowchart for an evaluation assistance process in accordance with the present embodiment. FIGS. 19 and 20 illustrate further examples of the trained model list screen. FIG. 21 is an explanatory diagram for a method of generating evaluation information. The processes depicted in FIG. 18 are performed by, for example, the service providing apparatus 5 executing a predetermined program.

Upon the processes depicted in FIG. 18 being started, the service providing apparatus 5 acquires, from the usage apparatus 6, an examination image 50, examination label information, and a condition required to be satisfied by a trained model (step S41). Then, the service providing apparatus 5 acquires a plurality of trained models 10 (step S42), generates a plurality of pieces of first identification information (step S43), generates a plurality of result images (step S44), and generates a plurality of pieces of first evaluation information (step S45). In particular, first identification information, a result image, and first evaluation information are generated for each of the trained models. Note that the processes of steps S41-S45 are similar to those of steps S21-S25 depicted in FIG. 12.

In addition, the service providing apparatus 5 acquires a plurality of sample images and a plurality of pieces of sample label information (step S46). The plurality of sample images are each an image used in a training process for a corresponding trained model of the plurality of trained models acquired in step S42. The plurality of pieces of sample label information each identify a correct answer region that is a positive or negative region included in each of the plurality of sample images. The pieces of sample label information are stored in the database in advance together with the trained models and the sample images. In step S46, a combination of at least one sample image and a piece of sample label information may be acquired for each trained model, or a combination of a plurality of sample images and pieces of sample label information may be acquired for each trained model. The following descriptions are given with reference to an example in which a combination of one sample image and a piece of sample label information is acquired for each trained model.

Upon acquiring a plurality of sample images and a plurality of pieces of sample label information, the service providing apparatus 5 generates a plurality of pieces of second identification information (step S47) and generates a plurality of reference images (step S48). The processes of steps S47 and S48 are similar to those of steps S36 and S37 depicted in FIG. 14.

Then, the service providing apparatus 5 generates a plurality of pieces of second evaluation information (step S49). Each of the plurality of pieces of second evaluation information is generated on the basis of each of the plurality of pieces of second identification information generated in step S47 and each of the plurality of pieces of sample label information acquired in step S46.

Second evaluation information is similar to first evaluation information except that second evaluation information is obtained by quantitatively evaluating a trained model 10 on the basis of sample label information. Thus, for example, second evaluation information may be a precision, a recall, a F-measure, a specificity, or an accuracy or may be a false negative rate or a false positive rate. Second evaluation information is not limited to a single indicator and may be an arbitrary combination of the plurality of indicators described above.

In step S49, the service providing apparatus 5 specifies regions corresponding to true positive, false positive, false negative, or true negative by comparing sample label information and second identification information, both specifying regions on an image. Upon these regions being specified, the service providing apparatus 5 calculates second evaluation information using the areas of these regions.

At least one sample image may be acquired for each trained model, or a plurality of sample images may be acquired for each trained model. When a plurality of sample images are acquired for each trained model, the values of a plurality of pieces of second evaluation information calculated from a plurality of pieces of sample label information corresponding to the plurality of sample images and the representative value of the plurality of pieces of second evaluation information may be calculated for each trained model. For example, the representative value may be an average or a median.

Finally, the service providing apparatus 5 outputs the plurality of result images, the plurality of pieces of first evaluation information, and the plurality of pieces of second evaluation information (step S50). In this case, the service providing apparatus 5 outputs each of the plurality of result images generated in step S44 after associating the result image with a corresponding trained model 10 of the plurality of trained models 10 selected in step S42, a piece of corresponding first evaluation information of the plurality of pieces of first evaluation information generated in step S45, a corresponding reference image of the plurality of reference images generated in step S48, and a piece of corresponding second evaluation information of the plurality of pieces of second evaluation information generated in step S49. In particular, the service providing apparatus 5 transmits a screen 600 depicted in FIG. 19 to the usage apparatus 6 so as to cause the display apparatus 6a of the usage apparatus 6 to display the screen 600. The screen 600 is a trained model list screen for the evaluation assistance system and displays a plurality of result images and reference images generated using a plurality of trained models 10, a plurality of pieces of first evaluation information associated with the plurality of result images, and a plurality of pieces of second evaluation information pertaining to the plurality of reference images, in a manner such that these images and pieces of information are arranged in order.

When a plurality of examination images are acquired, a plurality of result images are generated for each of a plurality of trained models 10. In this situation, one or more result images may be displayed for each of the trained models 10. For each of the plurality of trained models, one or more result images to be displayed may be selected on the basis of a plurality of pieces of first evaluation information calculated from the plurality of examination images and the representative value of the plurality of pieces of first evaluation information. For example, the highest, or the highest and one or more subsequent values, among F-measures calculated for the examination images may be selected, and one or more result images corresponding to the selected one or more F-measures may be displayed. Alternatively, for example, one or more result images corresponding to a piece of first evaluation information that is the closest to the representative value of the plurality of pieces of first evaluation information may be selected and displayed.

When there are a plurality of sample images and a plurality of pieces of sample label information for each of a plurality of learning-completed images 10, a reference image is generated for each combination of a sample image and a piece of sample label information. As a result, a plurality of reference images are generated for each of the trained models 10. In this situation, one or more reference images may be displayed for each of the trained models 10. For each of the plurality of trained models 10, one or more reference images to be displayed may be selected on the basis of a plurality of pieces of second evaluation information calculated from the plurality of sample images and the representative value of the plurality of pieces of second evaluation information. For example, the highest, or the highest and one or more subsequent values, among F-measures calculated for the sample images may be selected, and a reference image corresponding to the selected one or more F-measures may be displayed. Alternatively, for example, one or more reference images corresponding to a piece of second evaluation information that is the closest to the representative value of the plurality of pieces of second evaluation information may be selected and displayed.

The screen 600 depicted in FIG. 19 displays, below a model condition field 601, combinations of pieces of identification information (model IDs) of trained models, pieces of metadata (creator, cell type, method), result images, pieces of first evaluation information (scores), reference images, and pieces of second evaluation information (scores) which are arranged in order, the number of combinations being equal to the number of trained models selected in step S42. Step S50 may include a process of assigning priority levels to the plurality of combinations on the basis of the plurality of pieces of first evaluation information and the plurality of pieces of second evaluation information; and each of the plurality of result images may be output in accordance with the priority level after being associated with a corresponding trained model, corresponding first evaluation information, a corresponding reference image, and corresponding second evaluation information. In particular, an order in which the combinations are arranged on the screen 600 may be decided on in accordance with the assigned priority levels. A sort button provided on the screen 600 may be clicked to change the order of arrangement in accordance with a condition prioritized by the user.

For example, when first evaluation information and second evaluation information are indicators such as F-measures which correspond to more preferable results when being a higher value, the service providing apparatus 5 may assign higher priority levels to combinations that include first evaluation information and second evaluation information indicating a higher value. When first evaluation information and second evaluation information indicating lower values are indicators of more preferable results, the service providing apparatus 5 may assign higher priority levels to combinations that include first evaluation information and second evaluation information indicating lower values.

When a plurality of pieces of second evaluation information are generated for each trained model, priority levels may be determined for each trained model on the basis of a piece of second evaluation information indicating the highest value. In this case, as depicted in FIG. 19, a reference image corresponding to a piece of second evaluation information indicating the highest value may be displayed on the screen 600 for each trained model.

When a plurality of pieces of second evaluation information are generated for each trained model, priority levels may be determined for each trained model on the basis of a piece of second evaluation information indicating the lowest value. In this case, as depicted in FIG. 20, a reference image corresponding to a piece of second evaluation information indicating the lowest value may be displayed on the screen 600 for each trained model. Accordingly, the user can evaluate each of the trained models on the basis of the worst result, thereby preventing incorrect evaluations based on a good result obtained by chance from being given.

For example, the user may make a selection by using a radio button provided near a reference image so as to perform switching for each trained model as to which of the best result or the worst result is to be displayed. When a plurality of pieces of first evaluation information are generated for each trained model, i.e., when a plurality of validation images are provided for each trained model, the best results and the worst results may be displayed in a switchable manner for result images, as in the case of reference images. A selection may be made to display medium results in addition to best and worst results. Fair evaluation can be given using medium results without being affected by chance.

When the system 1 performs the evaluation assistance process in accordance with the present embodiment, a plurality of result images are output as in the first embodiment. Accordingly, the user can check the difference between a recognition result indicated by each result image and a recognition result compliant with his/her standards for evaluation, so that the user can grasp the goodness of fit of each trained model to the user's purpose.

In the present embodiment, a plurality of pieces of first evaluation information are output together with a plurality of result images, as in the second embodiment. Thus, the user can quantitatively compare and evaluate a plurality of trained models by using the plurality of pieces of first evaluation information, so that a trained model fitting the user's purpose can be specified more easily.

In the present embodiment, a plurality of reference images are output together with a plurality of result images, as in the third embodiment. Accordingly, the user can grasp the intention of the model provider by checking the reference images, so that a trained model fitting the user's purpose can be specified more accurately.

In the present embodiment, in addition, a plurality of pieces of second evaluation information are output together with a plurality of pieces of first evaluation information. Accordingly, the reliabilities of the pieces of first evaluation information can be evaluated by comparing the pieces of first evaluation information and the pieces of second evaluation information, so that a trained model fitting the user's purpose can be specified more accurately.

The fourth embodiment has been described with reference to an example in which both first and second evaluation information are generated, but only second evaluation information may be generated and output. In this case, information pertaining to trained models and including result images may be output in accordance with priority levels assigned on the basis of second evaluation information. The second and fourth embodiments have been described by referring to examples in which the display apparatus 6a displays generated evaluation information, but evaluation information does not necessarily need to be displayed and may be used only to, for example, determine priority levels.

Meanwhile, the second and fourth embodiments have been described by referring to examples in which as depicted in FIG. 21, examination label information L1 obtained by identifying all positive or negative regions included in an examination image 50 is compared with first identification information so as to calculate first evaluation information. However, the task of specifying all positive or negative regions included in the examination image 50 could impose a large burden on the user. Accordingly, for example, examination label information L2 such as that depicted in FIG. 21 obtained by partially identifying (i.e., by identifying some of) at least either the positive regions or negative regions included in the examination image 50 may be compared with first identification information so as to calculate first evaluation information. Using such examination label information L2 allows the task burden on the user to be significantly reduced. The user may generate examination label information L2 by specifying only important portions directly linked to evaluation of trained models (e.g., portions for which an incorrect determination should be strongly avoided, portions for which it is highly difficult to make a determination). Thus, first evaluation information would not be diluted by information of relatively low importance, so that more proper evaluations can be given on the basis of first evaluation information. Although examination label information has been exemplified by referring to FIG. 21, sample label information obtained by partially identifying at least either the positive regions or negative regions included in a sample image may be used. In this case, the burden on the model provider can be significantly reduced.

Although the above-described embodiments are based on examples in which a plurality of trained models are compared and evaluated, the service providing apparatus 5 may assist the evaluating of a single trained model. In particular, the service providing apparatus 5 may output result images and reference images that correspond to a single trained model. Outputting associated result images and reference images allows the user to check the intention of the model provider and the difference between a recognition result indicated by each result image and a recognition result compliant with his/her standards for evaluation, so that the user can grasp the goodness of fit of each trained model to the user's purpose.

Although descriptions have been given of examples in which the service providing apparatus 5 provides services for assisting the usage apparatus 6 evaluating trained models, services provided by the service providing apparatus 5 are not limited to these examples. The service providing apparatus 5 may provide services for assisting the model providing apparatus evaluating trained models. The following describes an example in which the model providing apparatus provisionally registers trained models in the service providing apparatus 5 and evaluates the provisionally registered trained models by using services provided by the service providing apparatus 5. The provisional registration refers to registering a trained model in the database of the service providing apparatus 5 without making this model open to the public. Thus, the model providing apparatus can evaluate trained models thereof before making these models open to public.

Figure 22:
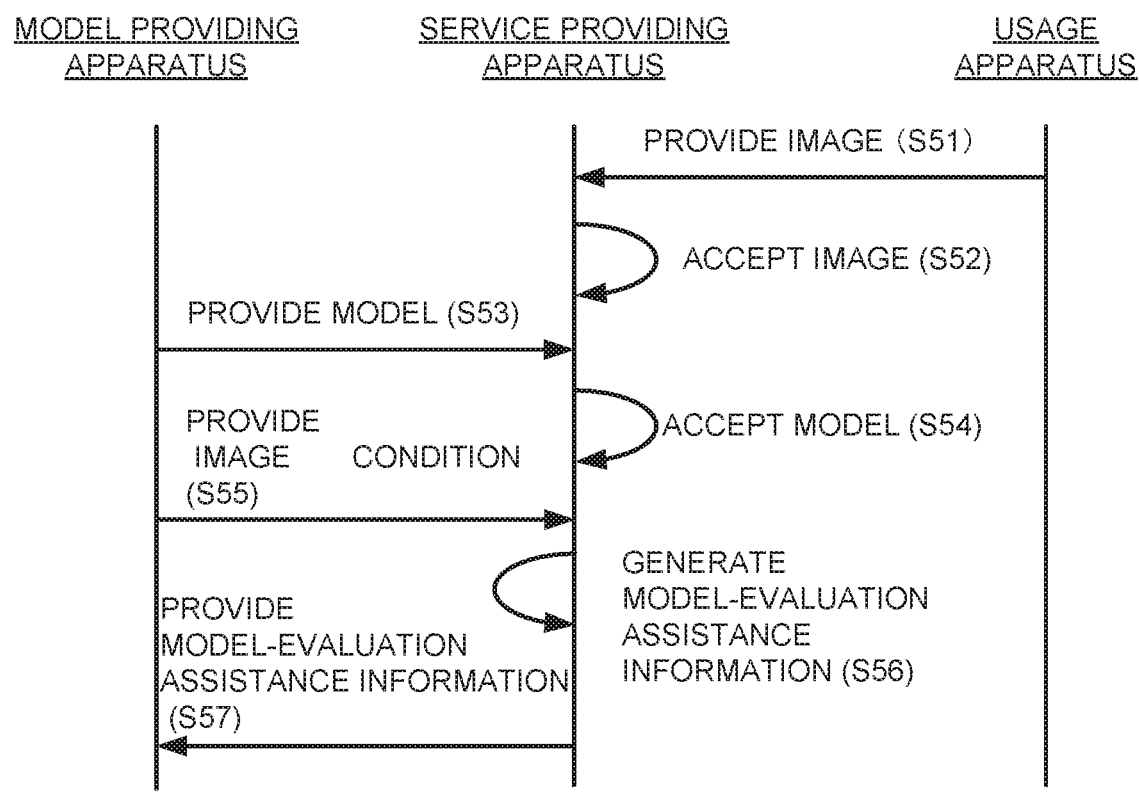
FIG. 22 is another example of a sequence diagram for illustrating services provided by a system 1.
Figure 23:
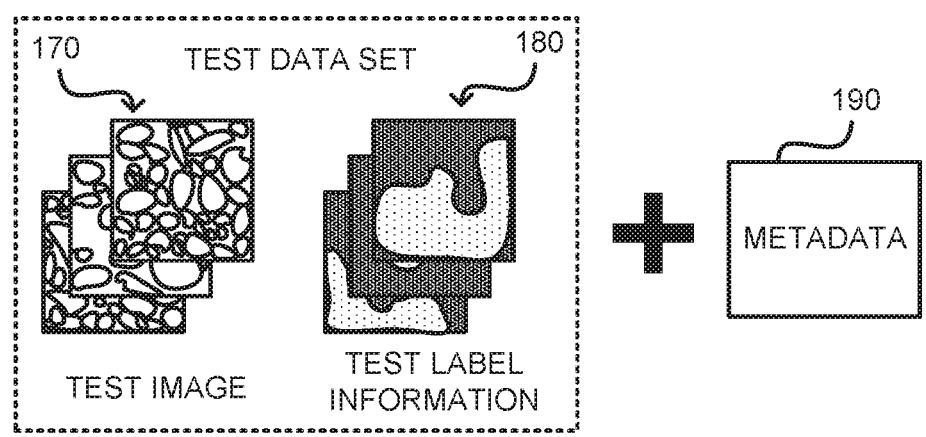
FIG. 23 is an explanatory diagram for data provided by a usage apparatus.

FIG. 22 is another example of a sequence diagram for illustrating services provided by the system 1. FIG. 23 is an explanatory diagram for data provided by the usage apparatus. By referring to FIGS. 22 and 23, the following describes a trained model evaluation assistance method implemented by the system 1.

In the system 1, the usage apparatus 6 first provides the service providing apparatus 5 with a test image 170 (step S51). As an acceptance condition, the service providing apparatus 5 has made in advance a request for the usage apparatus 6 to provide test label information 180 and metadata 190 together with a test image 170. Thus, in step S51, the usage apparatus 6 provides the service providing apparatus 5 with a test image 170, test label information 180, and metadata 190 in accordance with the acceptance condition, as depicted in FIG. 23. The test image 170 and test label information 180 form a test data set.

The test image 170 is an example of a first image prepared for performance evaluation of a trained model. The user of the usage apparatus 6 can provide the service providing apparatus 5 with test images 170 for performance evaluation of unknown trained models, thereby increasing the possibility of the service providing apparatus 5 being provided with trained models appropriate for data (test image) provided by the user.

The test label information 180 provided by the usage apparatus 6 indicates a correct answer as an output associated with an input of the test image 170. Thus, for example, test label information 180 may be identification information identifying a correct answer region that is a positive or negative region included in a test image 170.

Metadata 190 provided by the usage apparatus 6 is used when selecting test data to be used by the service providing apparatus 5 to evaluate a trained model. For a test image 170 that is an image of cells, metadata 190 may include, for example, a cell type, how cells have been acquired, whether gene transfer has been performed, and a culture condition. Metadata 190 may also include information on an apparatus that acquired the test image 170, such as an image capturing condition, an image size, and the number of images. In addition, metadata 190 may include information on whether a reagent or staining has been used, information on a reagent or staining condition, a standard for determining whether a region is positive or negative, or information on the creator of the image.

When a test image 170 is provided from the model providing apparatus, the service providing apparatus 5 accepts the provided test image 170 (step S52). In this case, the service providing apparatus 5 accepts and registers test label information 180 and metadata 190 as well as the test image 170 in a database built in a non-transitory computer-readable storage medium.

The image providing process in step S51 may be performed by a plurality of usage apparatuses, and thus a multitude of test images 170 may be registered in the service providing apparatus 5.

Then, to evaluate a trained model, the model providing apparatus first provides the service providing apparatus 5 with the trained model (step S53). The process of step S53 is similar to that of step S1 depicted in FIG. 3.

When a trained model is provided from the model providing apparatus, the service providing apparatus 5 accepts the provided trained model (step S54). In this case, the service providing apparatus 5 accepts and registers a training data set and metadata 40 as well as the trained model 10 in a database built in a non-transitory computer-readable storage medium without making them open to the public. In the process of step S54, the trained model 10 is registered without being made open to the public. Thus, the process of step S54 is similar to the process of step S2 depicted in FIG. 3 except for provisional registration.

Then, to evaluate the trained model provided to the service providing apparatus 5, the model providing apparatus provides the service providing apparatus 5 with an image condition (step S55). The image condition is a condition required to be satisfied by a test image 170 to be used to evaluate the trained model.

When the image condition is provided from the model providing apparatus, the service providing apparatus 5 generates model-evaluation assistance information (step S56). In this case, the service providing apparatus 5 searches metadata registered in the database on the basis of the image condition and extracts a plurality of test images 170 meeting the condition required to be satisfied according to demand from the model providing apparatus. In addition, the service providing apparatus 5 applies the test images to the trained model provided from the model providing apparatus so as to generate model-evaluation assistance information that includes a plurality of test results for the test images. Note that model-evaluation assistance information is information for assisting the model providing apparatus evaluating a trained model.

Upon generating model-evaluation assistance information, the service providing apparatus 5 provides the model providing apparatus with the model-evaluation assistance information (step S57). Then, by referring to the model-evaluation assistance information displayed on the display apparatus of the model providing apparatus, the user of the model providing apparatus, i.e., the model provider, evaluates the performance of his/her trained model.

In the system 1, as described above, the service providing apparatus 5 generates a plurality of test results by applying a plurality of test images to a trained model and provides the model providing apparatus with these test results. Thus, the model provider can evaluate the performance of his/her trained model by referring to the plurality of test results. The following describes specific examples of the processes of steps S55-S57 in FIG. 22 in detail with reference to embodiments.

Fifth Embodiment

Figure 24:
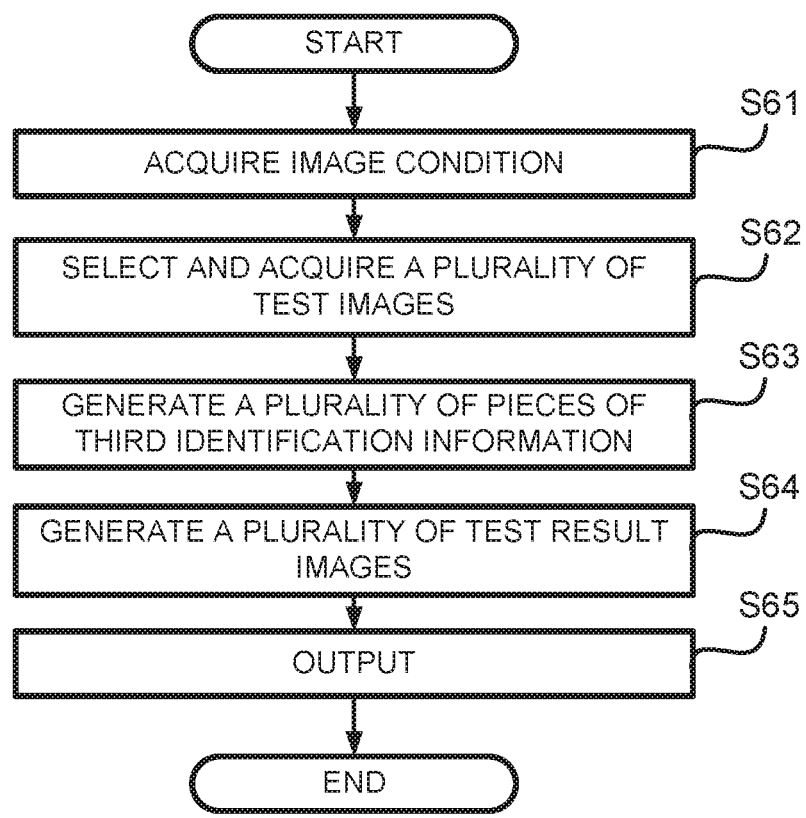
FIG. 24 is a flowchart for an evaluation assistance process in accordance with a fifth embodiment.
Figure 25:
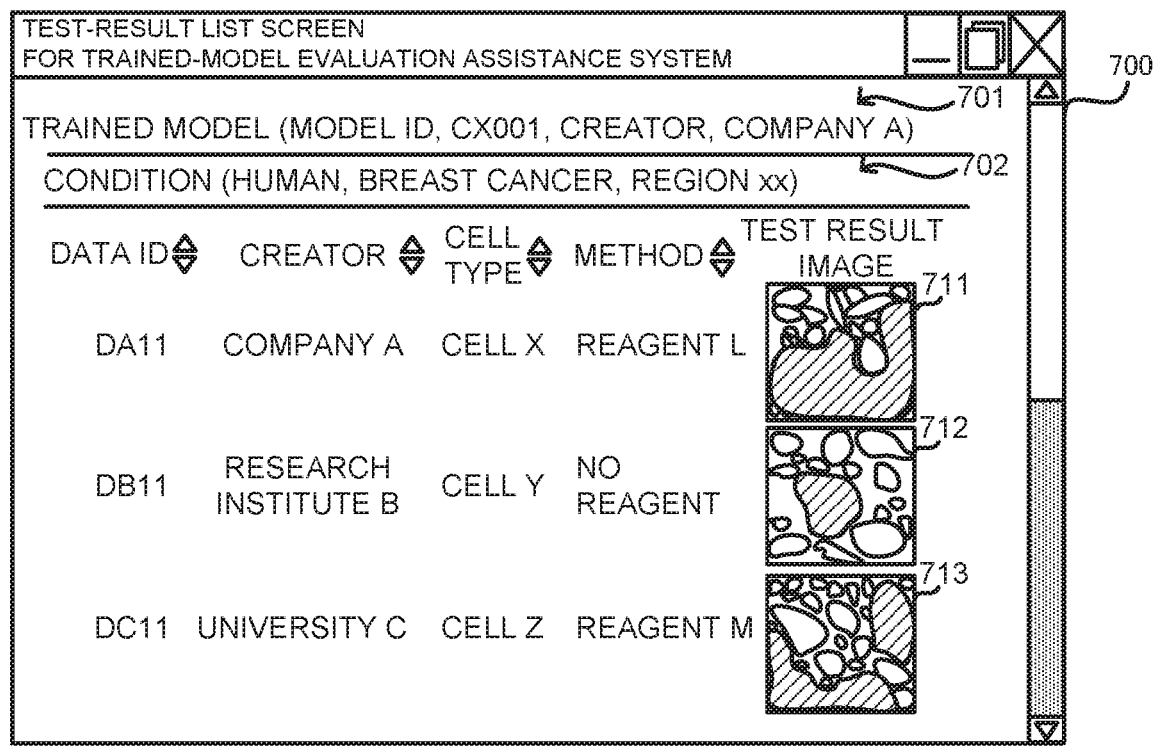
FIG. 25 illustrates an example of a test-result list screen.

FIG. 24 is a flowchart for an evaluation assistance process in accordance with the present embodiment. FIG. 25 illustrates an example of a test-result list screen. The processes depicted in FIG. 24 are performed by, for example, the service providing apparatus 5 executing a predetermined program.

Upon the processes depicted in FIG. 24 being started, the service providing apparatus 5 acquires an image condition provided from the model providing apparatus (step S61). In this case, for example, the model providing apparatus may access a website provided by the service providing apparatus 5, and in response to this, the service providing apparatus 5 may transmit an image-condition input screen to the model providing apparatus, thereby causing the display apparatus of the model providing apparatus to display the image-condition input screen. Subsequently, the model providing apparatus transmits an image condition input to the input screen by the model provider to the service providing apparatus 5, and the service providing apparatus 5 acquires the image condition. The following describes an example in which the service providing apparatus 5 has acquired "HUMAN, BREAST CANCER, REGION xx" as an image condition.

Then, the service providing apparatus 5 selects and acquires a plurality of test images 170 (step S62). In this case, on the basis of the image condition acquired in step S51, the service providing apparatus 5 searches metadata 190 registered in advance in the database in association with test images 170. Then, a plurality of test images 170 meeting the condition required to be satisfied according to demand from the model provider are extracted. Thus, step S62 is a process of acquiring a plurality of first images to be used for performance evaluation of a trained model.

Upon acquiring a plurality of test images 170, the service providing apparatus 5 generates a plurality of pieces of third identification information (step S63). In this case, the service providing apparatus 5 applies each of the plurality of test images 170 acquired in step S62 to the trained model 10 accepted in step S54 so as to generate a plurality of pieces of third identification information corresponding to the plurality of test images 170. As many pieces of third identification information as the number of test images 170 acquired in step S62 are generated. In this example, each of the plurality of pieces of third identification information identifies a region predicted to be a positive region by the trained model 10.

Then, the service providing apparatus 5 generates a plurality of test result images 710 (step S64). A test result image 710 is an example of a second image that is a result of processing a test image 170 by a trained model. In this case, the service providing apparatus 5 superimposes the plurality of pieces of third identification information generated in step S63 on the test images 170 acquired in step S62, thereby generating a plurality of test result images 710 (test result images 711, 712, and 713).

Finally, the service providing apparatus 5 outputs the plurality of test result images (step S65). In this case, the service providing apparatus 5 outputs each of the plurality of test result images generated in step S64 after associating the test result image with the trained model 10 accepted in step S54. In particular, the service providing apparatus 5 transmits a screen 700 depicted in FIG. 25 to the model providing apparatus so as to cause the display apparatus of the model providing apparatus to display the screen 700. Thus, step S65 is a process of displaying a trained model in association with a plurality of second images. The screen 700 is a test-result list screen for the evaluation assistance system and displays a plurality of test result images 710 generated using a plurality of test images 170 in a manner such that the test result images 710 are arranged in order.

The screen 700 depicted in FIG. 25 displays, below a model field 701 for displaying information on a trained model and an image condition field 702 for displaying information on an image condition, combinations of pieces of identification information (data IDs) of test images, pieces of metadata (creator, cell type, method), and test result images which are arranged in order, the number of combinations being equal to the number of test images selected in step S62. An order in which the combinations are arranged may be decided on the basis of the degree of conformity to a condition that the provider of the trained model requires to be satisfied. A sort button provided on the screen 700 may be clicked to change the order of arrangement in accordance with a condition prioritized by the model provider.

As described above, when the system 1 performs the evaluation assistance process in accordance with the present embodiment, test results for a plurality of test images provided by a third party are output as a plurality of test result images. Thus, the model provider can objectively evaluate his/her trained model by referring to the plurality of test result images. Accordingly, the evaluation assistance method in accordance with the present embodiment allows a creator to objectively evaluate, through validation using data provided by a third party, the performance of a trained model built by this creator.

Figure 26:
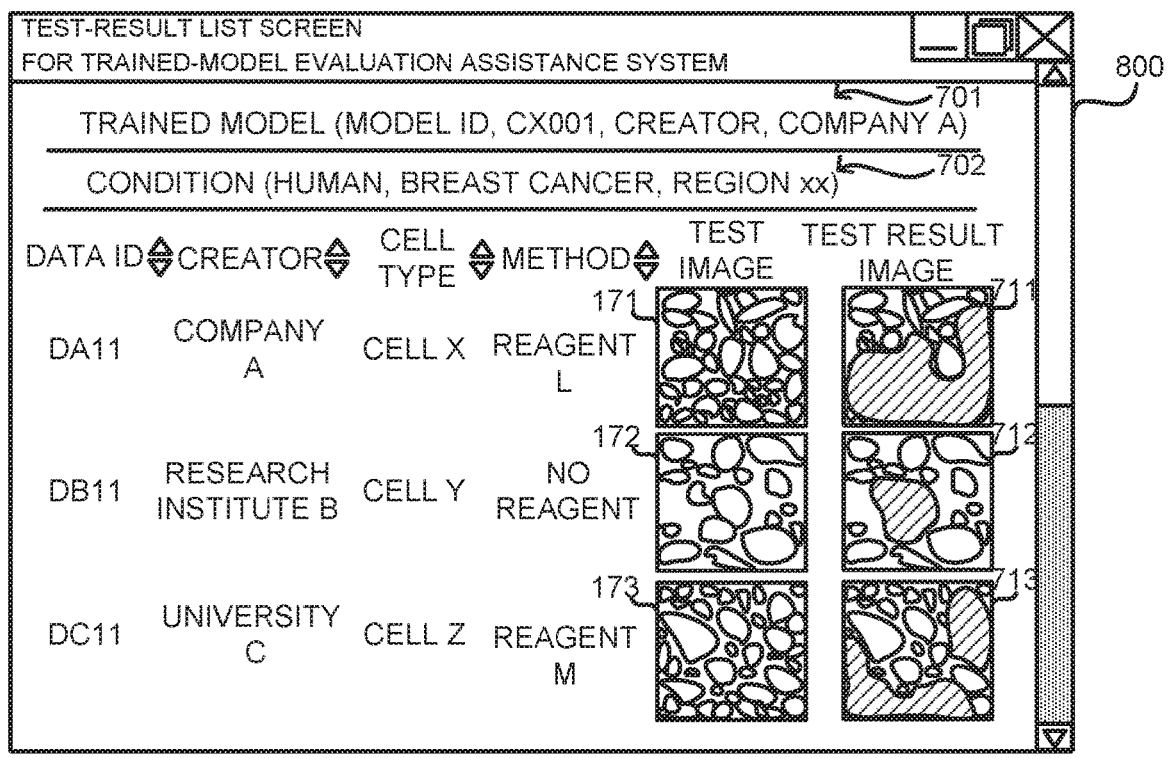
FIG. 26 illustrates another example of a test-result list screen.

In step S65, the system 1 may output a screen 800 depicted in FIG. 26, instead of the screen 700 depicted in FIG. 25. The screen 800 is different from the screen 700 in that test images 170 (test images 171, 172, and 173) are displayed adjacent to test result images 710 (test result images 711, 712, and 713). Thus, step S65 is a process of displaying each of the plurality of second images in association with a corresponding first image.

Displaying the screen 800 depicted in FIG. 26 allows the model provider to more clearly understand a test result for each test image so that trained models can be evaluated more properly.

Sixth Embodiment

Figure 27:
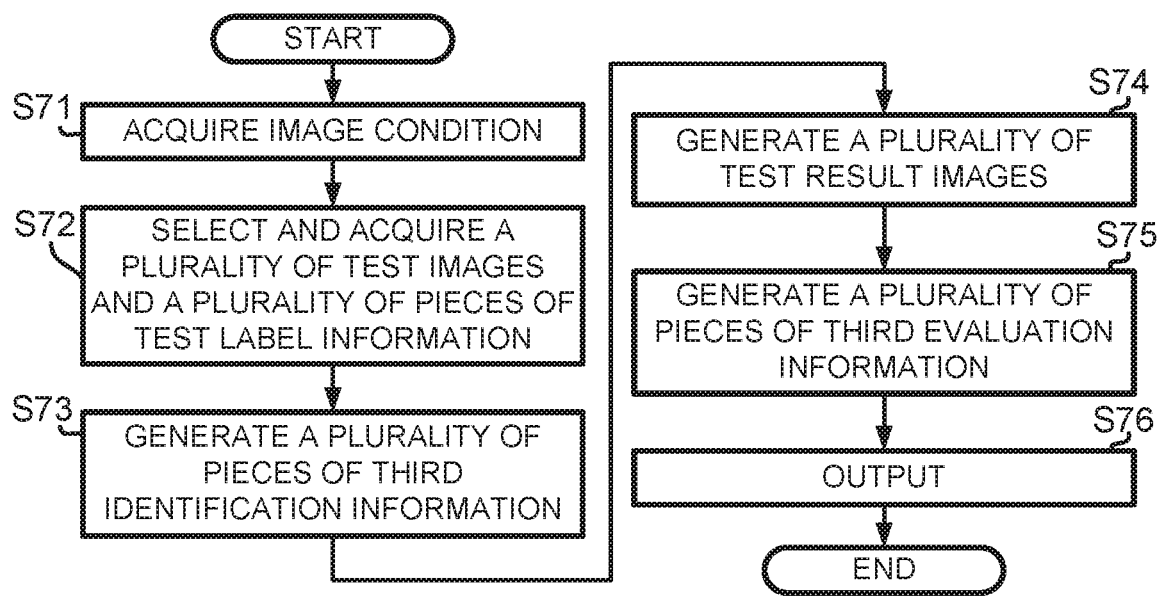
FIG. 27 is a flowchart for an evaluation assistance process in accordance with a sixth embodiment.
Figure 28:
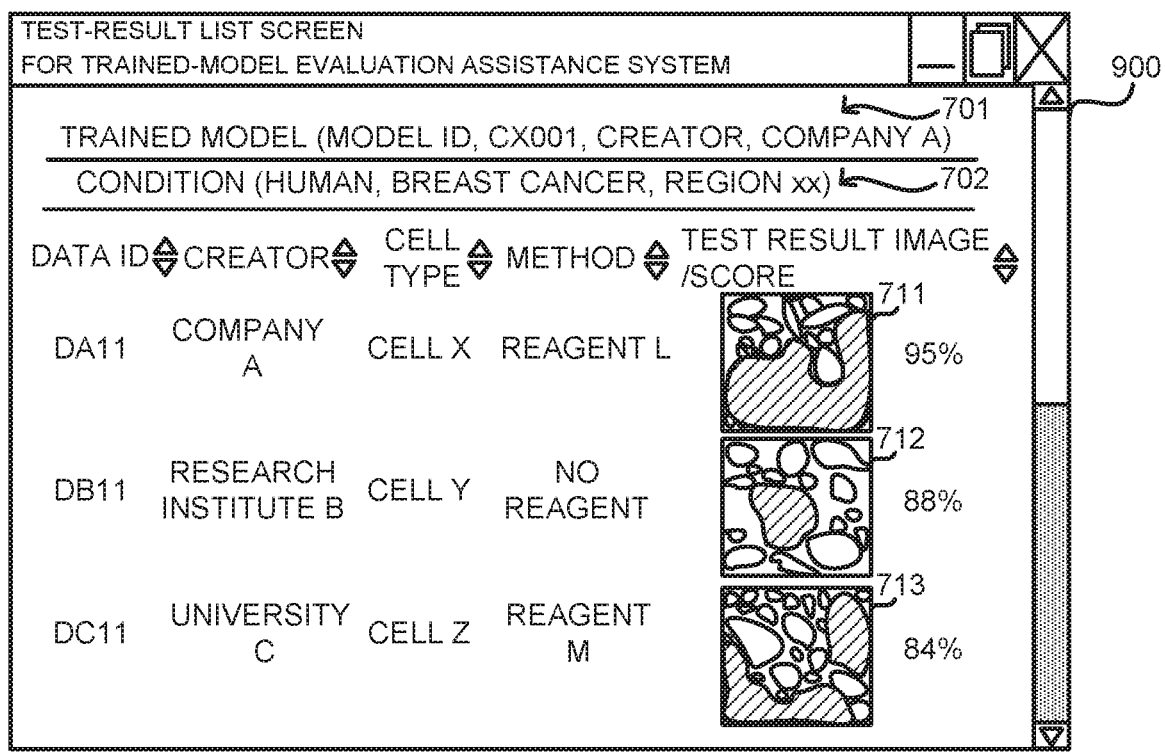
FIG. 28 illustrates still another example of a test-result list screen.

FIG. 27 is a flowchart for an evaluation assistance process in accordance with the present embodiment. FIG. 28 illustrates another example of a test-result list screen. The processes depicted in FIG. 27 are performed by, for example, the service providing apparatus 5 executing a predetermined program.

Upon the processes depicted in FIG. 27 being started, the service providing apparatus 5 acquires an image condition provided from the model providing apparatus (step S71). The process of step S71 is similar to that of step S61 depicted in FIG. 24.

Then, the service providing apparatus 5 selects and acquires a plurality of test images 170 and a plurality of pieces of test label information 180 (step S72). In this case, the service providing apparatus 5 acquires test images 170 and test label information 180 registered in association with the test images 170. The process of step S72 is similar to that of step S62 depicted in FIG. 24 except that test label information 180 is acquired.

Upon acquiring a plurality of test images 170, the service providing apparatus 5 generates a plurality of pieces of third identification information (step S73) and generates a plurality of test result images 710 (step S74). The processes of steps S73 and S74 are similar to those of steps S63 and S64 depicted in FIG. 24.

Then, the service providing apparatus 5 generates a plurality of pieces of third evaluation information (step S75). Each of the plurality of pieces of third evaluation information is generated on the basis of each of the plurality of pieces of third identification information generated in step S73 and apiece of corresponding test label information of the plurality of pieces of test label information acquired in step S72. Thus, the service providing apparatus 5 generates third evaluation information for each of the test result images 710.

As with first evaluation information, third evaluation information is, for example, a precision, a recall, or a F-measure which is a harmonic mean between the precision and the recall. Alternatively, third evaluation information may be a specificity or an accuracy. Also as in the case of first evaluation information, third evaluation information indicating a higher value is not necessarily more preferable. For example, third evaluation information may be a false negative rate or a false positive rate. Third evaluation information is not limited to a single indicator and may be an arbitrary combination of the plurality of indicators described above.

In step S75, the service providing apparatus 5 may calculate a representative value for the plurality of pieces of third evaluation information on the basis of the plurality of pieces of third evaluation information. For example, the representative value may be an average or a median.

Finally, the service providing apparatus 5 outputs the plurality of test result images and the plurality of pieces of third evaluation information (step S76). In this case, the service providing apparatus 5 outputs each of the plurality of test result images generated in step S74 after associating the test result image with the trained model 10 accepted in step S54 and a piece of corresponding third evaluation information of the plurality of pieces of third evaluation information generated in step S75. In particular, the service providing apparatus 5 transmits a screen 900 depicted in FIG. 28 to the model providing apparatus so as to cause the display apparatus of the model providing apparatus to display the screen 900.

The screen 900 is different from the screen 700 in that scores serving as third evaluation information are displayed adjacent to test result images 710 (test result images 711, 712, and 713).

As described above, when the system 1 performs the evaluation assistance process in accordance with the present embodiment, test results for a plurality of test images provided by a third party are output as a plurality of test result images and a plurality of scores. Thus, the model provider can objectively evaluate his/her trained model by referring to the plurality of test result images and the plurality of scores. Accordingly, the evaluation assistance method in accordance with the present embodiment also allows a creator to objectively evaluate, through validation using data provided by a third party, the performance of a trained model built by this creator. In particular, displaying a score together with a test result image allows this image to be quantitatively evaluated.

Figure 29:
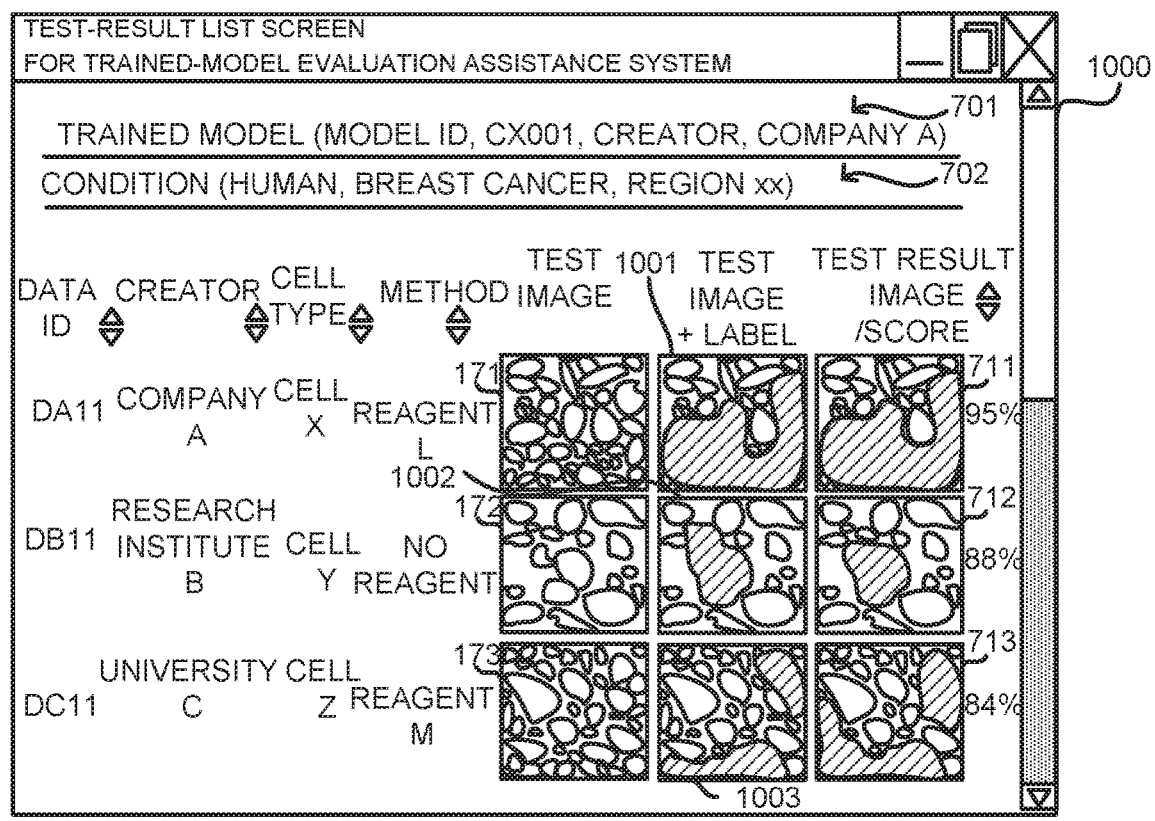
FIG. 29 illustrates yet another example of a test-result list screen.

In step S76, the system 1 may output a screen 1000 depicted in FIG. 29, instead of the screen 900 depicted in FIG. 28. The screen 1000 is different from the screen 900 in that test images 170 (test images 171, 172, and 173) and composite images (composite images 1001, 1002, and 1003) are displayed adjacent to test result images 710 (test result images 711, 712, and 713). Note that a composite image is obtained by superimposing test label information on a test image.

Displaying the screen 1000 depicted in FIG. 29 results in the displaying of information as bases for scores together with test results (test result images and scores) associated with individual test images, thereby allowing the model provider to more properly evaluate trained models.

Figure 30:
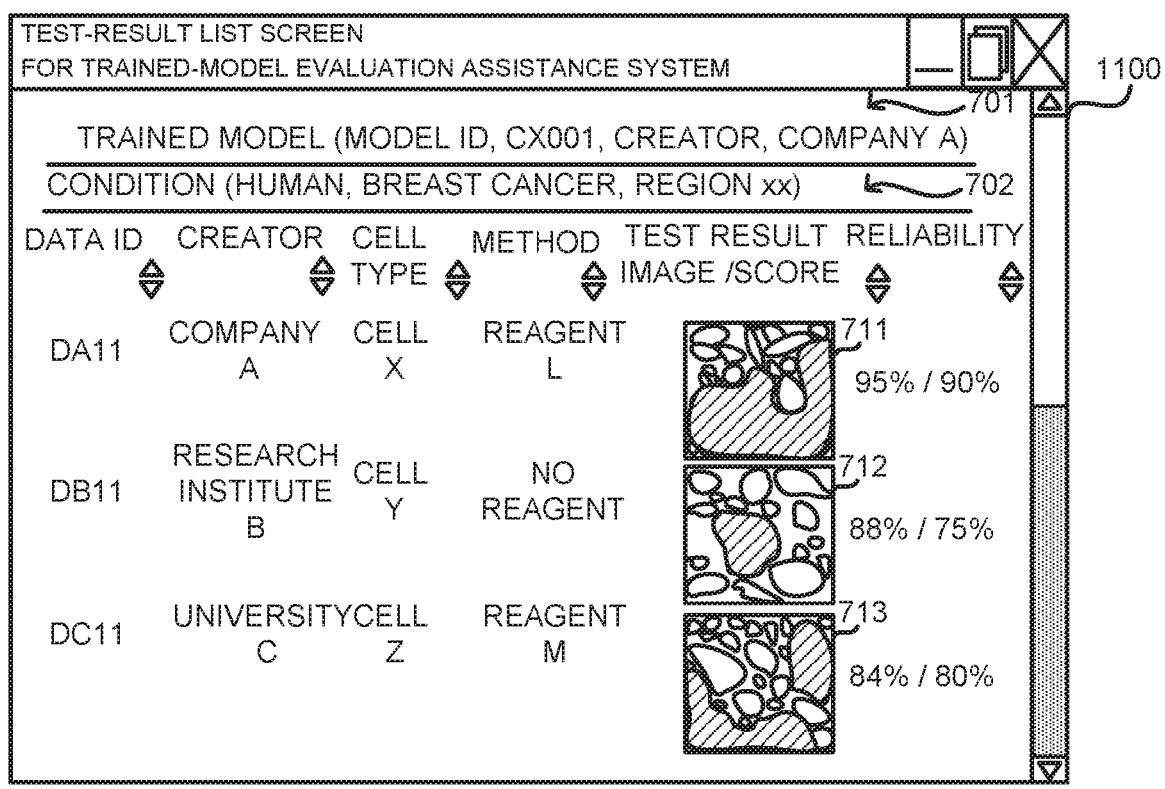
FIG. 30 illustrates a further example of a test-result list screen.

In step S76, the system 1 may output a screen 1100 depicted in FIG. 30, instead of the screen 900 depicted in FIG. 28. The screen 1100 is different from the screen 900 in that in addition to scores (third evaluation information), reliabilities are displayed adjacent to test result images 710 (test result images 711, 712, and 713). A reliability is the reliability of a test result image generated by a trained model, more specifically the reliability of third identification information output when the trained model generates a test result image.

Displaying the screen 1000 depicted in FIG. 30 allows the model provider to more clearly understand test results (test result image, score, and reliability) for each test image so that trained models can be evaluated more properly. In particular, displaying a score and a reliability allows a trained model to be evaluated in more detail. For example, when test result images with low scores are output, the model provider can make the performance evaluation of trained models different between the outputting with a high reliability and the outputting with a low reliability.

Figure 31:
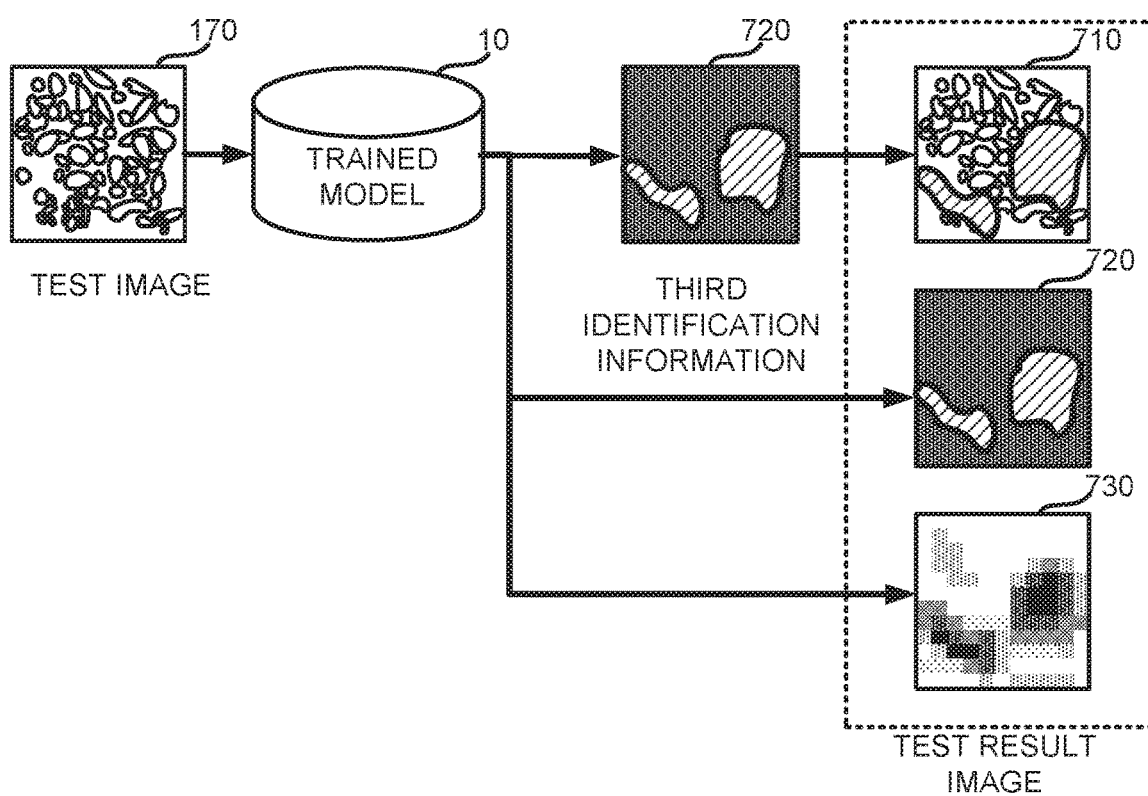
FIG. 31 is an explanatory diagram for a variation of a test-result image.

The fifth and sixth embodiments have been described with reference to examples in which the trained model 10 outputs third identification information 720 identifying a correct answer region and generates a test result image 710 by superimposing the third identification information 720 on a test image 710, but methods of generating a test result image are not limited to these examples. For example, third identification information 720 may be output as a test result image, as depicted in FIG. 31. In addition, a trained model 10 may generate a test result image 730 constituting a heat map, as depicted in FIG. 31. A test result image 730 may be generated by outputting, as reliabilities, the probabilities of individual regions in an image being a correct answer region and visualizing the reliabilities. Note that the result images and the reference images in the first to fourth embodiments are not limited to images generated by superimposing identification information on an examination image and a sample image but may be identification information or a heat map.

Figure 32:
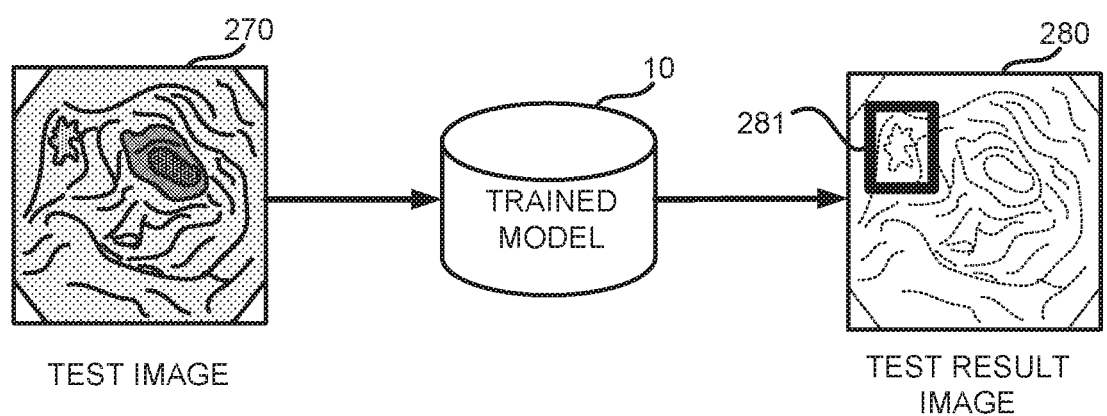
FIG. 32 is an explanatory diagram for a test-result image generated by a trained model of a detection type.

Embodiments have been described above by exemplifying trained models of a segmentation type wherein images are labeled on a pixel-by-pixel basis, but trained models are not limited to this type. Trained models may be of a detection type wherein the positions of elements within an image are specified as depicted in FIG. 32. FIG. 32 depicts an example in which a test image 270 that is an image of the inside of the body cavity acquired by an endoscope is input to a trained model 10 and a tumor is detected in the image. A test result image 280 output from the trained model 10 displays a frame 281 specifying the position of the tumor.

Figure 33:
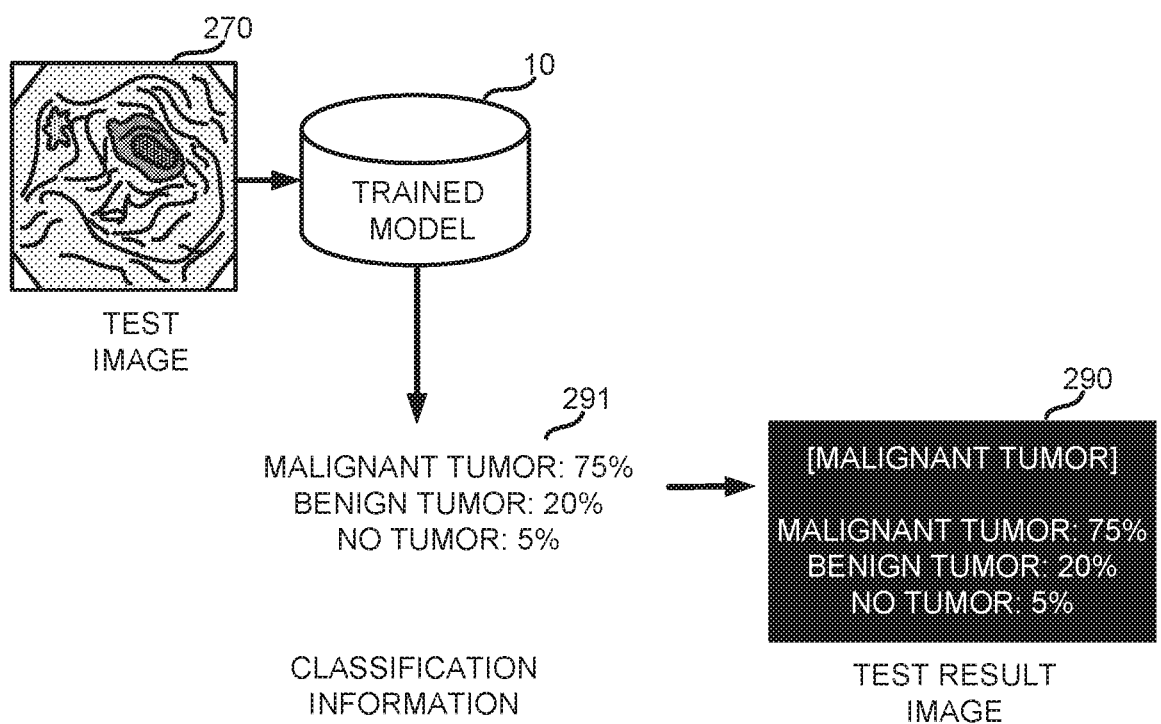
FIG. 33 is an explanatory diagram for a test-result image generated by a trained model of a classification type.

In addition, a trained model may be of a classification type wherein an image is classified, as depicted in FIG. 33. FIG. 33 depicts an example in which a test image 270 is input to a trained model 10 and classified with percentages indicated. The trained model 10 may output the classification information 291 as a test result image or output a test result image 290 obtained by converting the classification information 291 into an image. Alternatively, a graph expressing the percentages may be output as a test result image. In particular, a circle graph may be output, or a histogram describing various classification names on a horizontal axis and percentages for the classifications on a vertical axis may be output.

Embodiments have been described by referring to examples in which still images are dealt with, but trained models may deal with moving images. Moving images may be displayed on the screen. For example, an especially important portion of about a few seconds in a moving image may be repeatedly displayed, or an image display region may be clicked to start a moving image, e.g., the moving image may be replayed for a certain period such as a few seconds after the clicking. Displaying a moving image allows identification information to be referred to with information before and after a certain time, such as information on peristaltic movement of an organ or movement of cells, being reflected. An image of a portion of a moving image may be displayed, and in particular, only a certain frame of the moving image may be chosen and displayed as a still image. When using a moving image, a trained model that has learned the moving image in advance is used. When identification information could possibly be moved, a trained model of the detection type will desirably be used.

The embodiments described above indicate specific examples to facilitate understanding of the invention, and the present invention is not limited to these embodiments. Some of the embodiments described above may be applied to other embodiments. Various modifications or changes can be made to the trained model evaluation assistance method and evaluation assistance system and computer-readable medium without departing from the recitation in the claims.

In the fifth and sixth embodiments, the provider of trained models can evaluate his/her trained models without disclosing details of the trained models unnecessarily to many and unspecified users. In the first to fourth embodiments, the user of trained models can evaluate desired trained models without disclosing images acquired by the user unnecessarily to many and unspecified users. Thus, both providers and users can evaluate trained models without disclosing core information that needs to be kept secret. Accordingly, trained models appropriate for images such as medical images that need to be addressed in consideration of privacy protection can be searched for.

The following appendixes are further disclosed with reference to the above-described embodiments.

Appendix 1. An evaluation assistance method for trained models, the evaluation assistance method comprising:

acquiring an examination image input as an object to be examined;

generating a plurality of pieces of first identification information, the plurality of pieces of first identification information each being generated by applying the examination image to each of a plurality of trained models, the plurality of trained models each being a model for outputting identification information identifying a prediction region which is predicted to be a positive or negative region included in an image;

generating a plurality of result images, the plurality of result images each being generated by superimposing each of the plurality of pieces of first identification information on the examination image; and outputting each of the plurality of result images after associating the result image with a corresponding learning model of the plurality of trained models.

Appendix 2. The evaluation assistance method of appendix 1, further comprising:

acquiring a plurality of sample images, the plurality of sample images each being an image used in a training process for a corresponding learning model of the plurality of trained models;

generating a plurality of pieces of second identification information, the plurality of pieces of second identification information each being generated by applying, to each of the plurality of trained models, a corresponding sample image of the plurality of sample images; and generating a plurality of reference images, the plurality of reference images each being generated by superimposing each of the plurality of pieces of second identification information on a corresponding sample image of the plurality of sample images, wherein the outputting each of the plurality of result images includes outputting each of the plurality of result images after associating the result image with the corresponding learning model and a corresponding reference image of the plurality of reference images.

Appendix 3. The evaluation assistance method of appendix 1, further comprising:
acquiring examination label information identifying a correct answer region that is a positive or negative region included in the examination image; and
generating a plurality of pieces of first evaluation information, the plurality of pieces of first evaluation information each being generated on the basis of each of the plurality of pieces of first identification information and the examination label information, wherein
the outputting each of the plurality of result images includes outputting each of the plurality of result images after associating the result image with the corresponding learning model and a piece of corresponding first evaluation information of the plurality of pieces of first evaluation information.

Appendix 4. The evaluation assistance method of appendix 2, further comprising:
acquiring examination label information identifying a correct answer region that is a positive or negative region included in the examination image;
acquiring a plurality of pieces of sample label information, the plurality of pieces of sample label information each identifying a correct answer region that is a positive or negative region included in each of the plurality of sample images;
generating a plurality of pieces of first evaluation information, the plurality of pieces of first evaluation information each being generated on the basis of each of the plurality of pieces of first identification information and the examination label information; and
generating a plurality of pieces of second evaluation information, the plurality of pieces of second evaluation information each being generated on the basis of each of the plurality of pieces of second identification information and each of the plurality of pieces of sample label information, wherein
the outputting each of the plurality of result images includes outputting each of the plurality of result images after associating the result image with the corresponding learning model, a corresponding reference image of the plurality of reference images, a piece of corresponding first evaluation information of the plurality of pieces of first evaluation information, and a piece of corresponding second evaluation information of the plurality of pieces of second evaluation information.

Appendix 5. The evaluation assistance method of appendix 3, further comprising:
assigning priority levels to a plurality of combinations on the basis of the plurality of pieces of first evaluation information, the plurality of combinations each being a combination of a result image, a piece of first evaluation information, and a learning model that correspond to each other, wherein
the outputting each of the plurality of result images includes outputting each of the plurality of result images in accordance with the priority levels after associating the result image with the corresponding learning model and the piece of corresponding first evaluation information.

Appendix 6. The evaluation assistance method of appendix 4, further comprising:
assigning priority levels to a plurality of combinations on the basis of the plurality of pieces of first evaluation information and the plurality of pieces of second evaluation information, the plurality of combinations each being a combination of a result image, a reference image, a piece of first evaluation information, a piece of second evaluation information, and a learning model that correspond to each other, wherein
the outputting each of the plurality of result images includes outputting each of the plurality of result images in accordance with the priority levels after associating the result image with the corresponding learning model, the corresponding reference image, the piece of corresponding first evaluation information, and the piece of corresponding second evaluation information.

Appendix 7. The evaluation assistance method of appendix 3, wherein
when a plurality of examination images are input, result images to be output are selected on the basis of whether first evaluation information indicates a high value or a low value, the first evaluation information being generated for each of the plurality of examination images.

Appendix 8. The evaluation assistance method of appendix 4, wherein
when a plurality of validation images and a plurality of sample images are input, result images and reference images to be output are selected on the basis of whether first evaluation information and second evaluation information indicate a high value or a low value, the first evaluation information and the second evaluation information being generated for each of the plurality of validation images and sample images.

Appendix 9. The evaluation assistance method of any one of appendixes 1-8, further comprising:
selecting the plurality of trained models from trained models registered in advance on the basis of metadata associated with the trained models registered in advance.

Appendix 10. An evaluation assistance system for trained models, the evaluation assistance system comprising:
a non-transitory computer-readable storage medium storing a plurality of trained models; and
at least one processor, wherein
the processor performs the processes of
acquiring an examination image input as an object to be examined,
generating a plurality of pieces of first identification information, the plurality of pieces of first identification information each being generated by applying the examination image to each of a plurality of trained models, the plurality of trained models each being a model for outputting identification information identifying a prediction region which is predicted to be a positive or negative region included in an image,
generating a plurality of result images, the plurality of result images each being generated by superimposing each of the plurality of pieces of first identification information on the examination image, and
outputting each of the plurality of result images after associating the result image with a corresponding learning model of the plurality of trained models.

Appendix 11. An evaluation assistance system for trained models, the evaluation assistance system comprising:
a non-transitory computer-readable storage medium storing a plurality of trained models; and
at least one processor, wherein
the processor performs the processes of
acquiring an examination image input as an object to be examined,
acquiring a plurality of sample images, the plurality of sample images each being an image used in a training process for a corresponding learning model of the plurality of trained models, generating a plurality of pieces of first identification information, the plurality of pieces of first identification information each being generated by applying the examination image to each of a plurality of trained models, the plurality of trained models each being a model for outputting identification information identifying a prediction region which is predicted to be a positive or negative region included in an image, generating a plurality of pieces of second identification information, the plurality of pieces of second identification information each being generated by applying, to each of the plurality of trained models, a corresponding sample image of the plurality of sample images, generating a plurality of result images, the plurality of result images each being generated by superimposing each of the plurality of pieces of first identification information on the examination image, and generating a plurality of reference images, the plurality of reference images each being generated by superimposing each of the plurality of pieces of second identification information on a corresponding sample image of the plurality of sample images, and the process of outputting each of the plurality of result images includes outputting each of the plurality of result images after associating the result image with the corresponding learning model and a corresponding reference image of the plurality of reference images.

Appendix 12. The evaluation assistance system of appendix 10, further comprising:
a display apparatus, wherein
the display apparatus displays the result images and learning models that correspond to each other and have been associated with each other and output by the processor.

Appendix 13. The evaluation assistance system of appendix 12, further comprising:
a display apparatus, wherein
the display apparatus displays the result images, reference images, and learning models that correspond to each other and have been associated with each other and output by the processor.

Appendix 14. A program causing a computer to perform the procedures of:
acquiring an examination image input as an object to be examined;
generating a plurality of pieces of first identification information, the plurality of pieces of first identification information each being generated by applying the examination image to each of a plurality of trained models, the plurality of trained models each being a model for outputting identification information identifying a prediction region which is predicted to be a positive or negative region included in an image;
generating a plurality of result images, the plurality of result images each being generated by superimposing each of the plurality of pieces of first identification information on the examination image; and
outputting each of the plurality of result images after associating the result image with a corresponding learning model of the plurality of trained models.

Appendix 15. An evaluation assistance method for trained models, the evaluation assistance method comprising:
acquiring an examination image input as an object to be examined;
acquiring a trained model and a sample image, the trained model being a model for outputting identification information identifying a prediction region which is predicted to be a positive or negative region included in an image, the sample image being an image used in a training process for the trained model;
generating first identification information by applying the examination image to the trained model;
generating second identification information by applying the sample image to the trained model;
generating a result image by superimposing the first identification information on the examination image;
generating a reference image by applying the second identification information to the sample image; and
outputting the result image after associating the result image with the reference image.

What is claimed is:

1. An evaluation assistance method comprising:
acquiring a plurality of first images to be used for performance evaluation of trained models;
generating a plurality of second images based on each of the plurality of first images by each of a plurality of trained models;
generating a plurality of pieces of first evaluation information based on the plurality of second images;
assigning priority levels to a plurality of combinations based on the plurality of pieces of first evaluation information; and
displaying each of the plurality of trained models in association with at least one corresponding second image of the plurality of second images, at least one piece of a plurality of pieces of first label information and the plurality of combinations in an order of arrangement compliant with the priority levels,
wherein the plurality of pieces of first label information each indicate a desired result of processing of each of the plurality of first images, and
wherein the plurality of combinations comprises the trained model, at least one second image, and at least one piece of first evaluation information that correspond to each other.

2. The evaluation assistance method of claim 1,
wherein the displaying each of the plurality of trained models further comprises displaying each of the plurality of trained models in association with the at least one corresponding second image and at least one first image corresponding to the at least one second image, and
wherein the at least one first image is included in the plurality of first images.

3. The evaluation assistance method of claim 1,
wherein the displaying each of the plurality of trained models further comprises displaying each of the plurality of trained models in association with the at least one corresponding second image and metadata associated with a corresponding trained model of the plurality of trained models.

4. The evaluation assistance method of claim 3, further comprising:
assigning priority levels to a plurality of combinations on the basis of a plurality of pieces of metadata associated with the plurality of trained models, the plurality of combinations each being a combination of a trained model, at least one second image, and a piece of metadata that correspond to each other,
wherein the displaying each of the plurality of trained models comprises displaying the plurality of combinations in the order of arrangement compliant with the priority levels.

5. The evaluation assistance method of claim 1,
wherein the displaying each of the plurality of trained models includes displaying each of the plurality of trained models in association with the at least one corresponding second image and a reliability of each of the at least one second image.

6. The evaluation assistance method of claim 5, further comprising:
assigning priority levels to a plurality of combinations on the basis of a plurality of reliabilities corresponding to the plurality of second images, the plurality of combinations each being a combination of a trained model, at least one second image, and a reliability of each of the at least one second image that correspond to each other,
wherein the displaying each of the plurality of trained models comprises displaying the plurality of combinations in the order of arrangement compliant with the priority levels.

7. The evaluation assistance method of claim 6,
wherein the assigning the priority levels comprises assigning higher priority levels to combinations configured with a lower reliability.

8. The evaluation assistance method of claim 1, further comprising:
assigning priority levels to a plurality of combinations on the basis of a frequency of use of the plurality of trained models, the plurality of combinations each being a combination of a trained model, at least one second image, and at least one piece of first evaluation information that correspond to each other,
wherein the displaying each of the plurality of trained models comprises displaying the plurality of combinations in the order of arrangement compliant with the priority levels.

9. The evaluation assistance method of claim 1, further comprising:
for each of the plurality of first images, selecting at least one second image from the plurality of second images.

10. The evaluation assistance method of claim 1, further comprising:
acquiring a plurality of third images, the plurality of third images each being an image used in a training process for a corresponding trained model of the plurality of trained models; and
generating a plurality of fourth images, the plurality of fourth images each being a result of processing a corresponding third image of the plurality of third images by a corresponding trained model of the plurality of trained models,
wherein the displaying each of the plurality of trained models comprises displaying each of the plurality of trained models in association with a corresponding second image of the plurality of second images and a corresponding fourth image of the plurality of fourth images.

11. The evaluation assistance method of claim 1,
wherein the plurality of second images are each a heat map.

12. The evaluation assistance method of claim 1, further comprising:
selecting the plurality of trained models on the basis of metadata associated with the trained models.

13. The evaluation assistance method of claim 1,
wherein each of the plurality of trained models is of a segmentation type, a detection type, or a classification type.

14. An evaluation assistance method comprising:
acquiring a plurality of first images to be used for performance evaluation of trained models;
generating a plurality of second images based on each of the plurality of first images by each of a plurality of trained models;
generating a plurality of pieces of first evaluation information based on the plurality of second images;
assigning priority levels to a plurality of combinations based on a frequency of use of the plurality of trained models; and
displaying each of the plurality of trained models in association with at least one corresponding second image of the plurality of second images, at least one piece of a plurality of pieces of first label information and the plurality of combinations in an order of arrangement compliant with the priority levels,
wherein the plurality of pieces of first label information each indicate a desired result of processing of each of the plurality of first images, and
wherein the plurality of combinations comprises the trained model, at least one second image, and at least one piece of first evaluation information that correspond to each other.

15. The evaluation assistance method according to claim 14,
wherein the displaying each of the plurality of trained models further comprises displaying each of the plurality of trained models in association with the at least one corresponding second image and metadata associated with a corresponding trained model of the plurality of trained models.

16. The evaluation assistance method according to claim 14,
wherein the displaying each of the plurality of trained models includes displaying each of the plurality of trained models in association with the at least one corresponding second image and a reliability of each of the at least one second image.

17. An evaluation assistance method comprising:
acquiring a first image to be used for performance evaluation of trained models;
generating a plurality of second images based on the first image by each of a plurality of trained models;
acquiring a plurality of third images used in a training process for a corresponding trained model of the plurality of trained models;
generating a plurality of fourth images based on a corresponding third image of the plurality of third images by a corresponding trained model of the plurality of trained models; and
displaying each of the plurality of trained models in association with a corresponding second image of the plurality of second images and a corresponding fourth image of the plurality of fourth images.

18. The evaluation assistance method according to claim 17,
wherein the displaying each of the plurality of trained models further comprises displaying each of the plurality of trained models in association with the at least one corresponding second image and at least one first image corresponding to the at least one second image, and
wherein the at least one first image is included in the plurality of first images.

19. The evaluation assistance method according to claim 17,
wherein the displaying each of the plurality of trained models further comprises displaying each of the plurality of trained models in association with the at least one corresponding second image and metadata associated with a corresponding trained model of the plurality of trained models.

20. The evaluation assistance method according to claim 17,
wherein the displaying each of the plurality of trained models includes displaying each of the plurality of trained models in association with the at least one corresponding second image and a reliability of each of the at least one second image.

* * * * *